United States Patent [19]
Lind et al.

[11] Patent Number: 6,084,075
[45] Date of Patent: Jul. 4, 2000

[54] AGONIST AND ANTAGONIST ANTIBODIES TO THE CHEMOKINE RECEPTOR-2 (CCR2)

[75] Inventors: Peter Lind, Uppsala, Sweden; Carlos Martinéz Alonso, Madrid, Spain; José Mario Mellado Garcia, Madrid, Spain; José Miguel Rodriguez Frade, Madrid, Spain

[73] Assignees: Pharmacia & Upjohn AB, Stockholm, Sweden; Consejo Superior de Investigaciones, Madrid, Spain

[21] Appl. No.: 08/734,171

[22] Filed: Feb. 28, 1997

[30] Foreign Application Priority Data

Mar. 1, 1996 [SE] Sweden .................................. 9600820

[51] Int. Cl.$^7$ ............................ C07K 16/24; C12N 15/02
[52] U.S. Cl. .............................. 530/388.22; 530/388.23; 530/389.2; 530/389.6; 435/70.21; 435/7.1; 435/7.2; 435/334; 435/326; 435/331; 435/335; 424/143.1; 424/145.1; 424/158.1
[58] Field of Search ................... 530/388.22, 388.23, 530/389.2, 389.6; 424/143.1, 145.1, 158.1; 435/70.21, 7.1, 7.2, 334, 326, 331, 335

[56] References Cited

U.S. PATENT DOCUMENTS

| 5,652,133 | 7/1997 | Murphy et al. ........................ 532/351 |
| 5,707,815 | 1/1998 | Charo et al. ............................ 435/7.2 |

FOREIGN PATENT DOCUMENTS

| WO 94/11504 | 5/1994 | WIPO ............................ C12N 15/12 |
| WO 05/19436 | 7/1995 | WIPO ............................ C12N 15/12 |
| 9623668 | 8/1996 | WIPO . |

OTHER PUBLICATIONS

Charo et al, *Proc. Natl. Acad. Sci.*, vol. 91, 1994, 2752–56.
Blood, Ala Al–Aoukaty et al., vol. 87, 1996, 4255–60.
Eur. J. Immunol. Shixin Qin et al., vol. 26, 1996, 640–47.
Cell, Kuldeep Neote et al., vol. 72, 1993, 415–425.
J. of Biol. Chem., J.M. Scot et al, vol. 270, No. 11, 1995, 5786–5792.
Charo et al, *PNAS 91* 1994, p. 2752–56.
Raport et al, *J. Leukocyte Biol* 59, 1996, p. 18.
Yamagome et al *BBPC* 202(2) 1994, p. 1156–62.
Su et al, *J Leukocyte Biol* 60, 1996, p. 658.
Szabo et al, *JBC* 220(43) 1995, p. 25348–51.
Receptor Molecular Biology vol. 25, Methods in Neurosurgery, ed Sealfan, Chapter 21, Ariano et al, p. 455–69, 1995.
Boring et al, *JBC* 271 (13) 1996, p. 7551–58.
Wu, et al, *JBC* 271 (49) p. 31202–09.
Horuk, *TIBS* vol. 15, May 1994, p. 159.
Baggiolini et al, *Annu Rev. Immunol* 1997, vol. 15 p. 675–705.
Acker et al, *Mediators of Inflammation* vol. 5, 1976, p. 393.
Howard et al, *TIBTECH* vol. 14, 1996, p. 46–5.
Zalallos et al, *BBRC* 1996, 227, p. 846–53.

*Primary Examiner*—Garnette D. Draper
*Attorney, Agent, or Firm*—Pollock, Vande Sande & Amernick, R.L.L.P.

[57] ABSTRACT

The invention relates to antibodies which is capable of binding the monocyte chemoattractant protein 1 (MCP-1) receptor CCR2, especially those which are capable of acting either as an antagonist or agonist. The claimed antobodies can be used for in vitro and/or in vivo diagnostic, for screening and detection of tissues and classes of cells expressing the MCP-1 receptor, for screening for new drugs and for therapeutic use. The invention also relates to a preparation comprising the claimed antibody and a microorganism or cell-line capable of producing the claimed antibody.

21 Claims, 19 Drawing Sheets

AGONIST AND ANTAGONIST ANTIBODIES TO THE CHEMOKINE RECEPTOR-2 (CCR2)

FIELD OF THE INVENTION

The present invention relates generally to antibodies which are capable of binding the monocyte chemoattractant protein 1 (MCP-1) receptor CCR2. More specifically, the present invention relates to agonists and antagonists acting on the receptors for the chemokine monocyte chemoattractant protein 1 (MCP-1) receptor CCR2, including antibodies, especially monoclonal antibodies, interacting with the extracellular regions of the MCP-1 receptors, which compete with MCP-1 and other natural ligands for receptor binding.

BACKGROUND OF THE INVENTION

The chemokines constitute a diverse group of small secreted basic proteins, that regulate the chemotactic migration and activation of a number of different leukocytes, particularly in the context of activation of the immune response during inflammatory conditions.

Examples of cells that have been shown to chemotactically respond to and become activated by the chemokines are neutrophils, eosinophils, basophils, monocytes, macrophages, as well as B lymphocytes and different types of T lymphocytes (Oppenheim, J. J., et al. (1991) Annu.Rev.Immunol. 9, 617–48; Miller, M. D. & Krangel, S. K. (1992) Crit.Rev.Immunol. 12(1,2) 17–46; Baggiolini, M., et al. (1994) Adv.Immunol. 55, 97–179).

The chemokines can be classified into two major groups based on the pattern of cysteinyl residues participating in disulfide bond formation in mature proteins. The first group, the CXC chemokines, or the a-chemokines, are characterized by the occurrence of two cysteinyl residues in the amino-terminal region, between which a different amino acid residue is positioned.

The second group, the CC chemokines, or the b-chemokines, are characterized by the occurrence of two adjacent cysteinyl residues occurring in the amino-terminal region.

A third, minor group of chemokines, represented by lymphotactin that has been isolated from mice and humans (Kelner, G. S., et al.(1994) Science 266, 1395–9; Kennedy, J., et al. (1995) J.Immunol. 155,203–9), is characterized by the occurrence of only two cystein residues, presumably forming a single disulfide bond in the mature protein. So far, these are the only representatives of the so-called c-type chemokines.

The CXC chemokines act primarily on neutrophils, in particular those CXC chemokines that carry the amino acid sequence Glu-Leu-Arg on their amino terminus. Examples of CXC chemokines that are active on neutrophils, are interleukin-8 (IL-8), GRO-α, -β, and -γ, NAP-2, ENA-78, and GCP-2.

The CC chemokines act on a larger variety of leukocytes such as monocytes, macrophages, eosinophils, basophils, as well as T and B lymphocytes. Examples of these are MCP-1, MCP-2, MCP-3, MIP-1α, MIP-1β, eotaxin, RANTES, I-309. The latter carries two additional cysteinyl residues probably forming a third disulfide bond in the mature protein.

MCP-1, or monocyte chemoattractant protein 1, was originally purified from phytohemagglutinin stimulated human lymphocytes (Yoshimura, T. et al. (1989) J.Immunol. 142, 1956–62), a human glioma cell line (Yoshimura, T., et al (1989) J.Exp.Med. 169, 1449–59), and the human myelomonocytic cell line THP-1 (Matsushima, K., et al. (1989) J.Exp.Med. 169, 1485–90). MCP-1 has also been called MCAF, LDCF, GDCF, HC11, TSG-8, SCYA2, and A2. Molecular cloning of the cDNA encoding MCP-1 (Furutani, Y., et al. (1989) Biochem.Biophys.Res.Comm. 169. 249–55; Rollins, B. J., et al. (1989) Mol. Cell. Biol. 9, 4687–95; Chang, H. C., et al. (1989) Int. Immunol. 1, 388–97) revealed an open reading frame of 99 amino acids, including a signal peptide of 23 amino acids.

MCP-1 is produced by monocytes, and a variety of tissue cells, such as endothelial cells, epithelial cells, fibroblasts, keratinocytes, synovial cells, mesangial cells, osteoblasts, smooth muscle cells, as well as by a multitude of tumour cells (Baggiolini, M., et al. (1994) Adv.Immunol. 55, 97–179, and references therein).

Its expression is stimulated by several types of pro-inflammatory agents, such as IL-1β, TNF-α, IFN-γ, lipopolysaccharide, and GM-CSF. MCP-1 is suggested to play an important role in the pathogenesis of atherosclerosis. Macrophages that are loaded with lipids, so-called foam cells, comprise the majority of cells in atherosclerotic lesions. It is suggested that active monocyte recruitment through MCP-1 from these cells and from activated endothelium plays a central role in the formation of fatty streaks and atherosclerotic plaques (Ylä-Herttuala, S., et al. (1991) Proc.Natl.Acad.Sci.USA 88(12), 5252–6; Schwartz, C. J., et al. (1993) Am. J. Cardiol. 71(6), 9B–14B;Takeya, M. (1993) Hum. pathol. 24(5), 534–9).

In the synovial fluid and plasma of patients with rheumatoid arthritis, the concentration of MCP-1 has been shown to be increased, as compared to other arthritic diseases, and the main source of this is macrophages which constitutively express MCP-1. In the rheumatoid synovium, MCP-1 together with other inflammatory cytokines such as IL-1β, IL-6, IL-8 and TNF-α, contribute to the immunopathogenesis of rheumatoid arthritis (Koch, A. E. (1992) J.Clin.Invest. 90, 772–79; Hosaka, S., et al. (1994) Clin.Exp.Immunol. 97, 451–7; Akahoshi, T., et al. (1993;) Arthritis.Rheum. 36, 762–71; Harigai, M., et al. (1993) Clin.Immunol.Immunopathol. 69, 83–91).

The mononuclear-phagocyte dependent lung injury mediated by IgA immune complexes is characterized by mononuclear and phagocytic cell accumulation, and has been shown to be largely dependent on the expression of MCP-1 (Jones, M. L., et al. (1992) J.Immunol. 149, 2147–54). Similarly, MCP-1 seems to play an important role in the pathogenesis of idiopathic pulmonary fibrosis and sarcoidosis (lyonaga, K., et al. (1994) Hum.Pathol. 25, 455–63; Car, B. D., et al (1994) Am.J.respir.Crit.Care.Med. 149, 655–9).

In animal models, MCP-1 has been shown to be expressed in the brain after focal ischemia (Kim, J. S., (1995) J.Neuroimmunol. 56, 127–34; Wang, X., et al. (1995) Stroke 26, 661–5), and during experimental autoimmune encephalomyelitis (Hulkower, K., et al. (1993) J.Immunol. 150, 2525–33; Ransohoff, R. M., et al. (1993) 7, 592–600). MCP-1 may be an important cytokine that targets mononuclear cells in the disease process illustrated by these animal models, such as stroke and multiple sclerosis.

In psoriatic lesions, MCP-1 seems to regulate the interaction between proliferating keratinocytes and dermal macrophages, and can be located above the dermal/epidermal junction. In addition to IL-8, which is important for the neutrophilic infiltration into these types of lesions, MCP-1 may serve to recruit mononuclear cells (Schroder, J. M. (1992) Arch. Dermatol. Res 284 Suppl 1, S22–6; Gillitzer, R., et al (1993) J.Invest.Dermatol. 101, 127–31).

MCP-1 seems to be involved in the control of mononuclear cell infiltration found in many solid tumors. A correlation between tumor associated MCP-1 production and the number and proliferative activity of tumor associated macrophages has been demonstrated (Walter, S., et al. (1991) Pathobiology 59(4), 239–42; Mantovani, A., et al. (1994) Adv.Exp.Med.Biol. 351, 47–54). Using transplanted sarcoma cells in mice, it has been demonstrated that cells expressing high levels of MCP-1 grow more slowly, and that this is related to the number of tumor associated macrophages (Walter, S., et al. (1991) Int.J.Cancer, 49, 431–5). Similarly, murine colon carcinoma cells engineered to express MCP-1, display reduced metastatic potential (Huang, S., et al. (1994) Cancer Immunol. Immunother. 39, 231–8).

MCP-1 is a powerful chemoattracting and activating factor for monocytes, inducing chemotaxis, calcium flux, and the respiratory burst, showing activity in the picomolar range (Yoshimura, T. & Leonard, E. J. (1990) J.Immunol. 154, 292–97; Zachariae, C. O. C., et al. (1990) J.Exp.Med. 171, 2177–82; Rollins, B., et al. (1991) Blood 78, 1112–6; Vaddi, K. & Newton, R. C. (1994) J.Leukoc.Biol. 55, 756–62). MCP-1 also upregulates CD11b/CD18 and CD11c/CD18 in a transient time course, which is likely to facilitate trans-endothelial migration during inflammation Oiang, Y, et al. (1992) J.Immunol. 148, 2423–8; Vaddi, K. & Newton, R. C. (1994) J. Immunol. 153, 4721–32).

It has recently become evident that in addition to monocytes, MCP-1 acts on CD4+ and CD8+ T lymphocytes as a chemoattractant both in vitro and in vivo (Loetscher, P., et al. (1994) FASEB J. 8, 1055–60; Carr, M. W., et al. (1994) Proc.Natl.Acad.Sci.USA 91, 3652–6; Taub, D. D., et al. (1995) 95, 1370–6). Natural killer cells that have been stimulated by interleukin-2, are also subject to chemotaxis by MCP-1 (Maghazachi, A.A., et al. (1994) J.Immunol. 153, 4969–77; Allaven, P., et al. (1994) Eur.J.Immunol. 24, 3233–6. This underscores the importance of this chemokine in the recruitment of effect of cells into inflammatory lesions.

In addition to the effects on monocytes and T lymphocytes, MCP-1 is a moderate chemoattractant and potent activator of allergy mediator release, such as histamine and leukotrienes, from basophils (Kuna, P., et al. (1992) J.Exp.Med. 175, 489–93; Bischoff, S. C., et al. (1992) J.Exp.Med. 175, 1271–7; Bischoff, S. C., et al. (1993) Eur. J. Immunol. 23, 761–7). In contrast to basophils, another granulocyte implicated in allergic inflammatory lesions, the eosinophil, does not respond to MCP-1 (Rot, A., et al (1992) J.Exp.Med. 176, 1489–95).

There exists one receptor for MCP-1, that seems to be expressed in two slightly different forms due to alternative splicing of the mRNA encoding the carboxy-terminal region, MCP-1-RA and MCP-1RB (Charo, I. F., et al. (1994) Proc.Natl.Acad.Sci.USA, 91, 2752–56).

These receptors (CCR2) are expressed in monocytes, myeloid precursor cells and activated T lymphocytes (Myers,S. J.,et al, 1995. *J. Biol. Chem.*, 270, 5786–5792, Qin, S. et al. 1996. *Eur. J. Immunol.* 26, 640–647). They provide an effective means of defining the molecular basis of chemokine-receptor interactions and of understanding MCP-1's role in the regulation of monocyte/macrophage infiltration in a variety of disease processes.

The MCP-1 receptor belongs to the seven transmembrane-type of proteins, and is homologous to the receptors for MIP-1α/RANTES (CC-CKR1; Neote, K. et al. (1993) Cell 72, 415–25) and Interleukin-8/GRO (Holmes, W. E., et al. (1991) Science 253, 1278–80; Murphy, P. M. & Tiffany, H. L. (1991) Science 253, 1280–3). The dissociation constant of MCP-1 to the receptor transfected into HEK-293 cells is 0.26 nM which is in agreement with values measured on monocytes (Myers, S. J. et al. (1995) J.Biol.Chem. 270, 5786–92; Van Riper, G. et al. (1993) J.Exp.Med. 177, 851–6). Activation of the MCP-1RB receptor on transfected HEK-293 cells by MCP-1 inhibits adenylyl cyclase at a concentration of 90 pM, and mobilizes intracellular calcium at slightly higher concentrations, seemingly independent of phosphatidyl inositol hydrolysis. The effects on adenylyl cyclase and intracellular calcium release are strongly inhibited by pertussis toxin, implying the involvement of Gi type heterotrimeric G-proteins in the signal transduction (Meyers S. J. et al, (1995) J. Biol. Chem. 270, 5786–92).

The recent description of chemokine receptors as HIV-1 coreceptors and of chemokines as neutralizing agents of HIV-1 infection, assigns these molecules a key role in HIV-1 pathogenesis (Doranz, B. J. et al. 1996, *Cell* 85, 1149–1158; Feng, Y et al. 1996. *Science* 272, 872–877; Deng, H et al, 1996. *Nature* 381, 661–666; Cocchi, F et al. 1995, *Science* 270, 1811–1815; Choe, H et al. 1996, *Cell* 85, 1135–1148; Alkhatib, G et al, 1996. *Science* 272,1955–1958). Specific tools are essential to aid in unravelling the manner in which chemokines and HIV-1 interact with the chemokine receptors, to determine which receptors are important in directing different HIV-1 strains to different peripheral blood mononuclear cell (PBMC) populations, and at what stage (binding, desensitization, signal transduction) this interaction takes place.

WO 95/19436, a patent application filed in the name of The regents of the University of California, describes an isolated DNA sequence that codes on expression for MCP-1 receptor. It is also mentioned that an antagonist of the MCP-1 receptor could be identified by expression of the N-terminal domain of MCP-1 receptor and detection of a loss in binding of the MCP-1 receptor domain. A pharmaceutical composition is claimed which comprises the MCP-1 receptor antagonist as identified by the disclosed method. No such identification is performed and no antagonists are isolated.

We have generated mAb specific for the CCR2 chemokine receptor by immunizing mice with synthetic peptides corresponding to several extracellular receptor domains. We describe the generation of mAb capable of specifically recognizing native CCR2 receptor. Analysis of CCR2 expression on human PBMC and tonsil cells shows its expression in B cells, which is thus added to its known expression in monocytes and activated T cells. This would suggest a role for MCP-1 in B cells. These mAb were characterized by their ability to block and/or mimic MCP-1 activity, based on chemotaxis and $Ca^{2+}$ induction in human monocytes and monocytic cell lines. Using these mAb, we define CCR2 regions critical for ligand binding and for eliciting a response through this receptor; we show a dissociation between these two activities that may help to unravel the complex mechanisms involved in chemokine signaling as well as the specificity relationship of these types of receptors. Based on the ability of these mAb to either trigger chemokine receptors or to block chemokine responses, we have outlined a model that takes into account our present knowledge of chemokine responses.

In contrast to IL-8 receptor neutralizing antibodies, which are directed to the $NH_2$ terminal region (37), our mAb with antagonist activity (MCPR-04 and MCP R-05) map to the third extracellular loop region of the CCR2 receptor. Another mAb with similar peptide specificity (MCP R-03), although it binds to the receptor, do not block the MCP-1 activity. The neutralizing activity of these antibodies is thus limited to the recognition of a few key residues within this region, which play a critical role in chemokine binding or in the modulation of chemokine activity. Earlier studies conclude on the importance of the chemokine receptor NH$_2$ terminal domain for the IL-8R, a member of the CXC chemokine receptor family. Several explanations may account for this difference. First, the structural features controlling CC chemokine interaction with its receptor may be distinct those of the CXC chemokines, and the present implication of the third extracellular domain might reflect this difference; neutralizing antibodies to other CC receptors must be tested before formal conclusions can be reached. Second is the surprising fact that amino terminal-specific mAb, for example MCP R-02, can mimic the chemokine response. This allows us to consider this region critical in agonist activation of the CCR2 receptor.

We therefore conclude that chemokine receptors are organized into two distinct functional domains, corresponding to the NH$_2$ terminal and third extracellular loop regions. All known chemokine receptors have a high degree of sequence identity and many chemokines can interact with more than one chemokine receptor. It is thus probable that ligand-receptor interactions involve similar regions in the distinct receptors, but effecting different modifications in the NH$_2$ terminal domain implicated in signal transduction. Our findings could thus be extrapolated to the entire chemokine receptor family and contribute to an explanation of the degeneracy in chemokine-chemokine receptor signalling.

In the experimental part below we describe the generation of mAbs that are capable of recognizing native MCP-1 receptor, and their characterization including their ability to block and/or mimetize the MCP-1 and induction of Ca$^{2+}$ in human monocytes and monocytic cell lines and chemotaxis.

SUMMARY OF THE INVENTION

The invention relates to an antibody, preferably a monoconal antibody, which is capable of binding the monocyte chemoattractant protein (MCP-1) receptor CCR2 as defined in the attached claims. Antibodies according to the claims recognize the extracellular aminoterminal region of the receptor and recognize sequences present in the third extracellular loop of the receptor.

The claimed antibody can be used for in vitro and/or in vivo diagnostic purposes and for therapeutic use.

Other aspects of the invention include the use for screening and detection of tissues and classes of cells expressing the MCP-1 receptor and for screening new drugs, e.g. new anti-inflammatory drugs.

For example, radiolabelled antibodies capable of binding to the MCP-1 receptor can be used to visualize areas of active inflammatory processes in the whole body in vivo, where there are accumulation of cellular species carrying MCP-1 receptors on their surfaces. Also, heterogeneous cell populations can be analysed in vitro for the occurrence of species of cells expressing the MCP-1 receptor by use of immunofluorescence microscopy or fluorescence activated cell sorting. Another use of antibodies binding to specific regions of the receptor, as exemplified in the experimental part, is for the in vitro screening of low molecular weight substances capable of interacting with the receptor in such a way as to displace these antibodies. For example, antibodies binding to the amino-terminal extracellular domain of the receptor, can be radioactively labelled, fluorescence labelled, enzymatically labelled, or labelled with an affinity tag, in such a way as these antibodies can interact with biochemically purified MCP-1 receptor preparations immobilized in wells in plastic dishes. Displacement of these antibodies by low molecular weight compounds could be measured by detection of residual bound antibody or released antibody. Similarly, antibodies interacting with other extracellular regions of the MCP-1 receptor could be used for screening of other compounds affecting the binding of these antibodies. Low molecular weight compounds displacing the antibodies can be expected to do so by binding to the extracellular regions of the MCP-1 receptor, and thereby possess either agonistic and/or antagonistic properties. Low molecular weight antagonistic compounds can be expected to constitute potential anti-inflammatory properties when administrated in vivo, and be useful as new drugs in the treatment of inflammatory conditions.

The invention also relates to an antibody preparation comprising the claimed antibody and to pharmaceutical composition preparation comprising the claimed antibody and a carrier.

The preparation comprises the antibody in a therapeutically effective amount together with a pharmaceutically acceptable carrier. The carrier is chosen depending on the route of administration. Suitable carriers are well known in the art.

This preparation, possible together with a carrier, may have a potential therapeutic use, especially when treating diseases such as inflammation, rheumatoid arthritis, mononuclear-phagocyte dependent lung injury, idiopathic pulmonary fibrosis, sarcoidosis, focal ischemia, autoimmune encephalomyelitis, stroke, multiple sclerosis, psoriatic lesions, tumor and chronic transplant rejection by administration of the claimed antibody to the patient in need thereof.

As the receptor for MCP-1 is present on the CD4+ and CD8+ T cells the claimed antibody can be active in a lymphocyte mediated destruction of specific cells, such as tumour cells or virally infected cells causing for example, AIDS.

The antibody is used for manufacture of a pharmaceutical preparation for treatment of the diseases disclosed above.

The antibody which is an agonist for the MCP-1 receptor could also be used in a bispecific antibody in which one part is directed to a cell or an HIV-infected cell and the other part is the agonist. Reference regarding bispecific antibody is given to e.g. A L Howell et al, J. Leukoc. Biol. 1994, Mar 55(3); 385–91 and Haagen I. A. et al, Cancer. Immunonol. Immunother. 1994, dec. 39(6); 391–6.

A micro-organism or cell-line capable of producing the claimed antibody are also part of the invention.

Chimeric or other recombinant antibodies capable of binding the MCP-1 receptor as well as fusion protein derivatives, conjugation derivatives or fragmented derivatives of these antibodies, are part of the invention.

The special antibodies MCPR-01, MCPR-03 and MCPR-06 as described below are useful for the characterization of the receptor and MCPR-02 is a receptor agonist and MCPR-04 and MCPR-05 are receptor antagonists.

Mab MCPR-02 could be used to neutralize HIV-1 infection, and mAb MCPR-04 and MCPR-05 could be used to block MCP-1 induced HIV-1 neutralization.

We have also used these mAb to identify the CCR2 receptor in several leucocyte populations and to identify the polarization of this receptor in lymphocytes. These mAb could also be of use in identifying conformational changes in CCR2 receptors following activation.

By using the sequences identified by us in the two distinct functional domains the antibodies can be prepared by a person skilled in the art.

BRIEF DESCRIPTION OF THE FIGURES

FIG. 4b shows the effect of MCPR-02 mAb dilution on Mono-Mac-1 cells migration under the same condition.

Figure 1A:
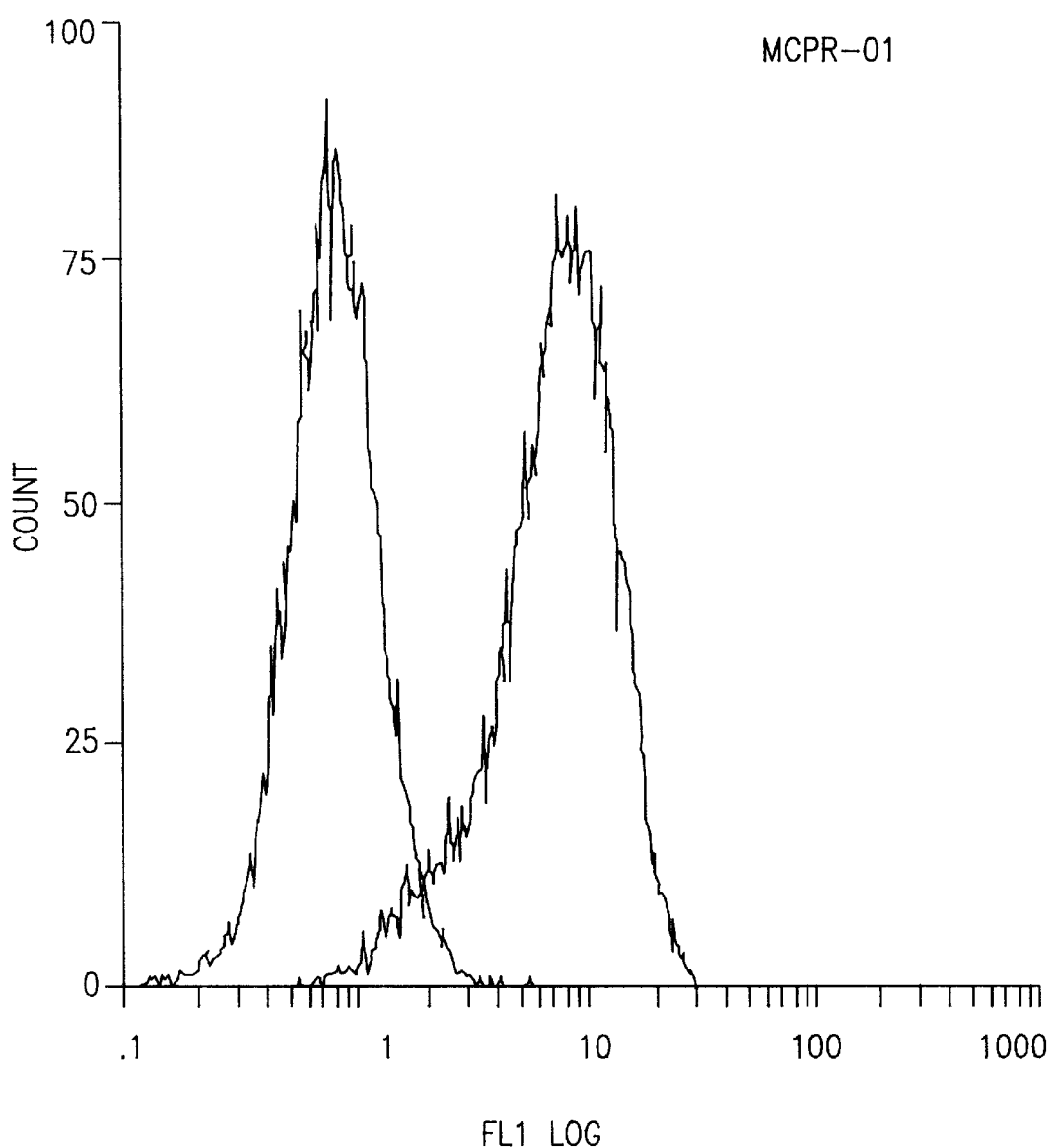
FIGS. 1a to 1f show the binding of selected monoclonal antibodies to Mono-Mac-1 cells using fluorescence activated cell sorting. Each figure shows binding of one of the monoclonal antibody MCPR-01 to MCPR-06, respectively.
Figure 1B:
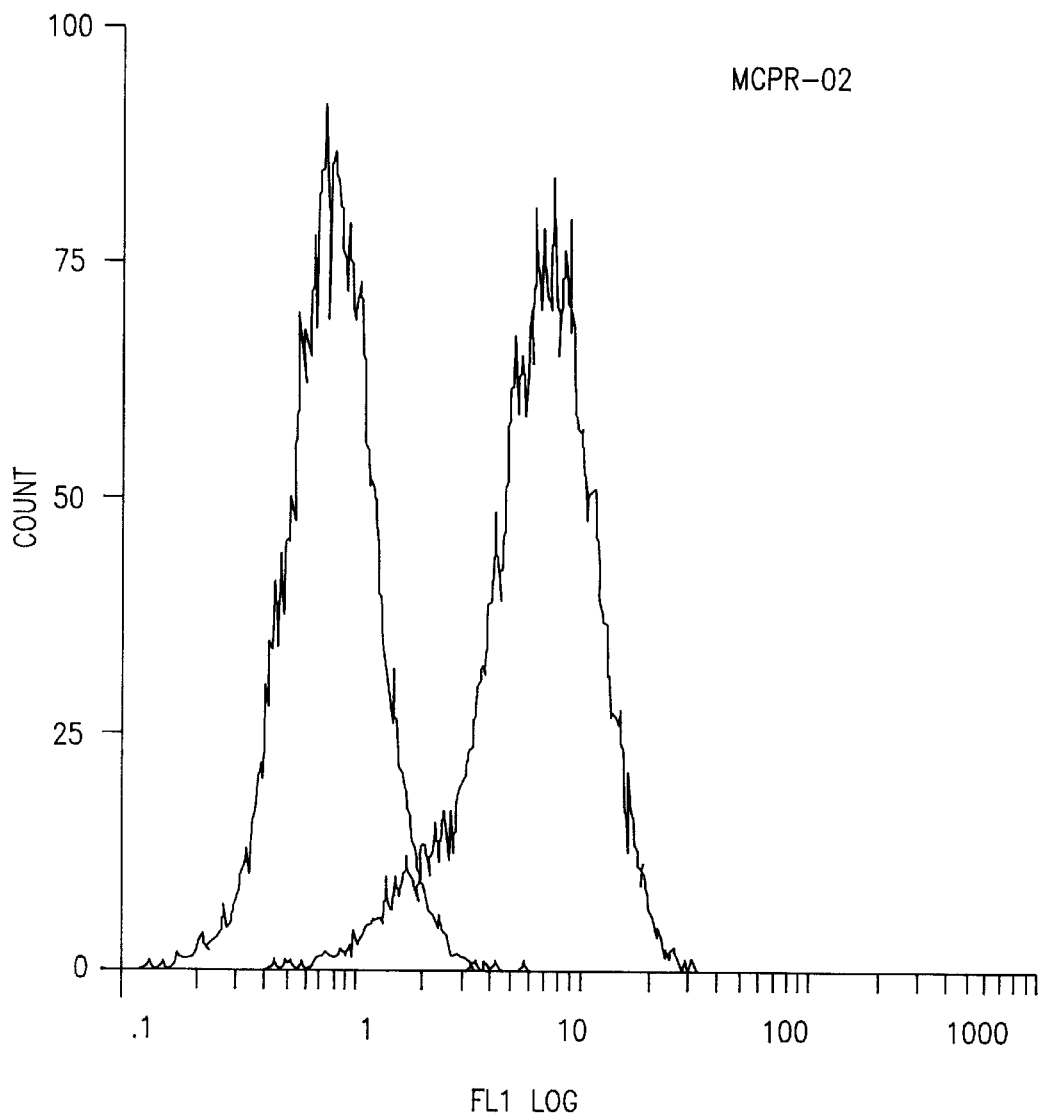
Figure 1C:
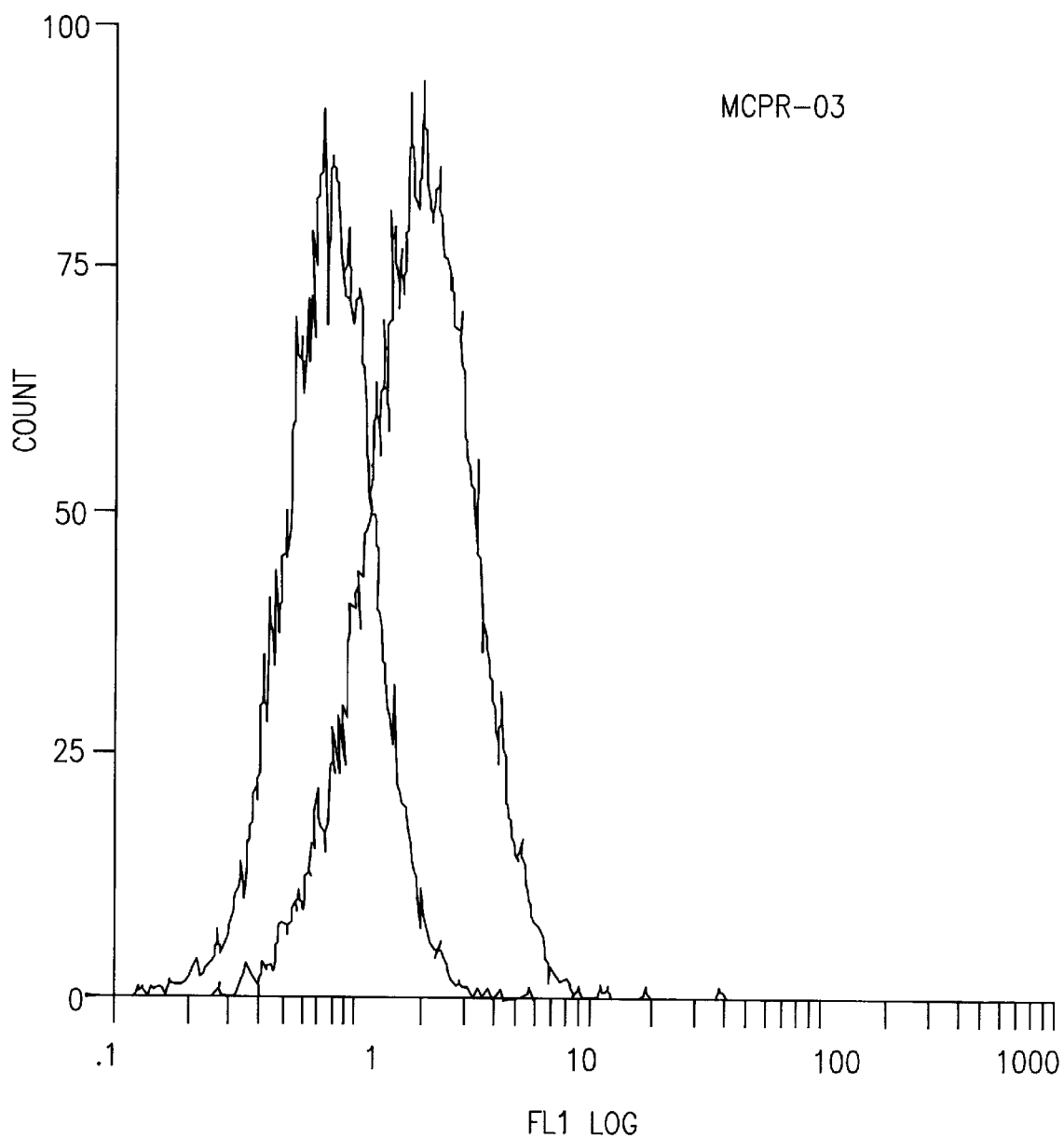
Figure 1D:
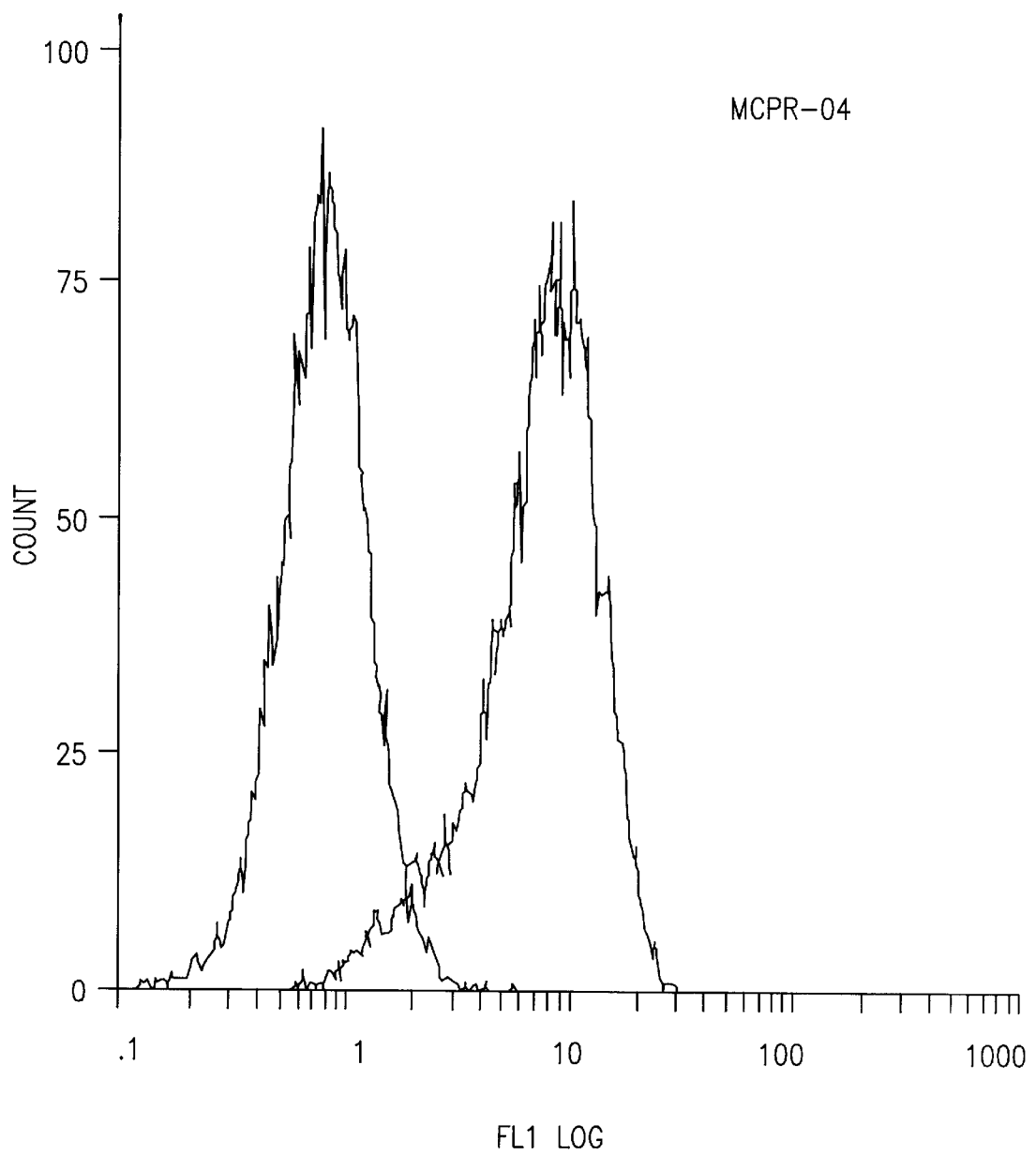
Figure 1E:
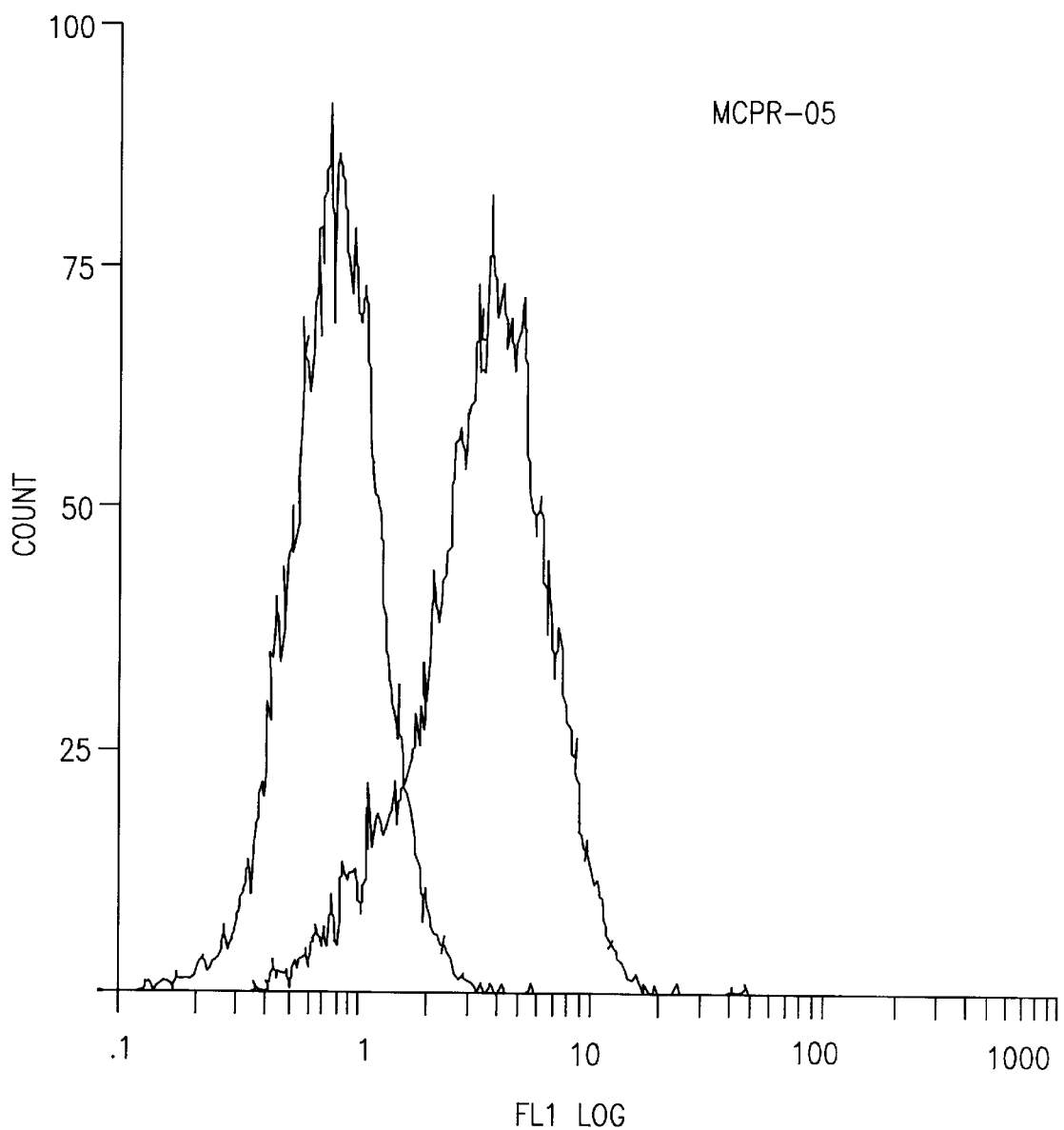
Figure 1F:
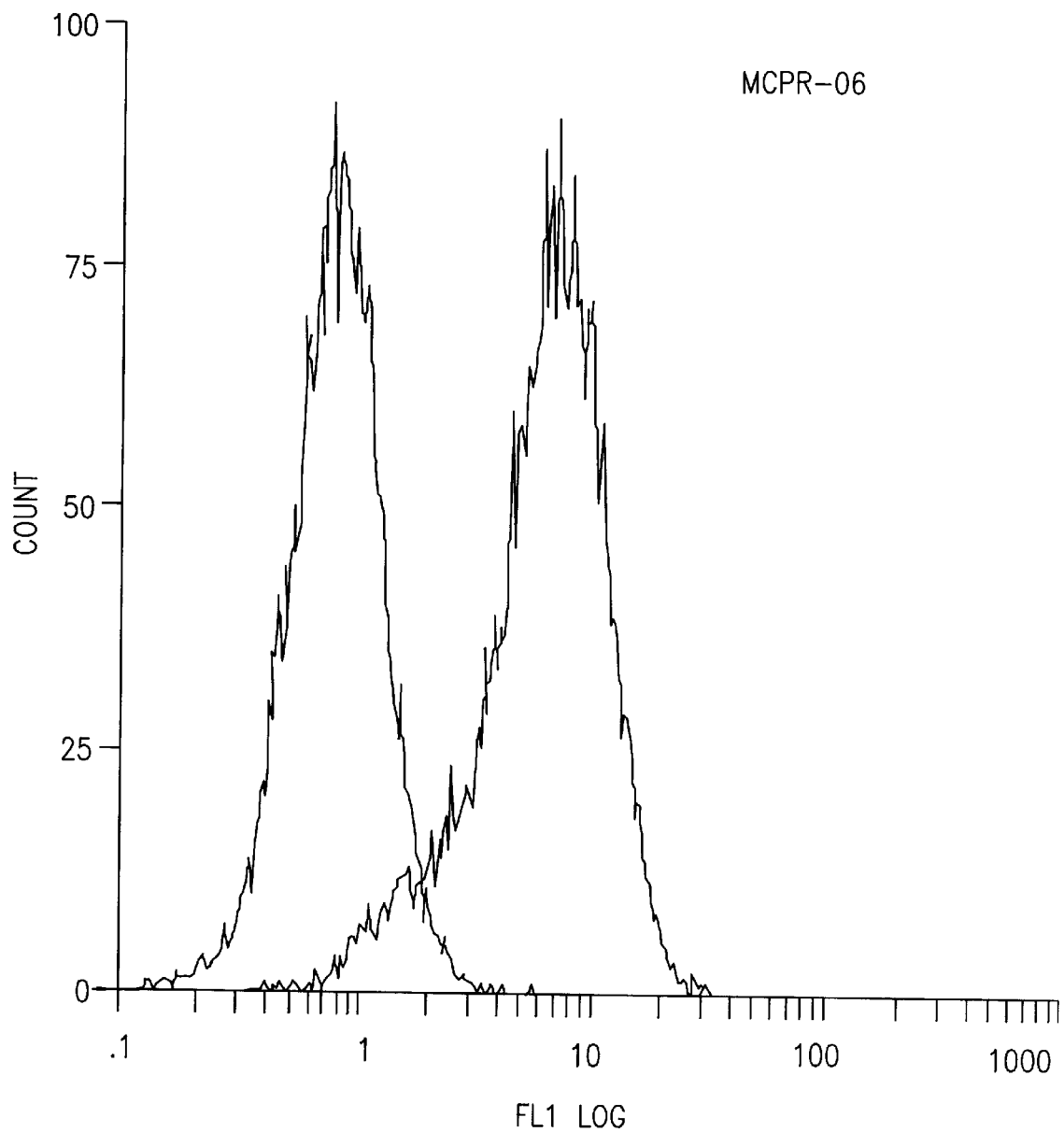

Tables I to III illustrate the invention.

DETAILED DESCRIPTION OF THE INVENTION

| DEFINITIONS | |
|---|---|
| BSA | Bovine Serum Albumin |
| CD11b and c | surface antigens |
| DMF | dimethyl formamide |
| DMSO | Dimethyl sulfoxide |
| ECL | Enzymatic Chamiluminescense |
| ED1 | A mouse monoclonal antibody recognizing rat monocytes from Serotec |
| ED2 | A mouse monoclonal antibody recognizing rat macrophages from Serotec |
| EIA | enzyme-linked immunoassay |
| FACS | fluorescence activated cell sorting |
| FCS | Foetal Calf Serum |
| FITC | Fluorescein isothiocyanate |

| -continued | |
|---|---|
| DEFINITIONS | |
| GM-CSF | Granulocyte and Macrophage Colony Stimulating factor |
| HIV | Human Immunodeficiency virus |
| IFN-γ | Interferon-γ |
| IL-1β | interleukine |
| KLH | Keyhole Limpet Hemocyanin, Pierce |
| MCP-1RB | Monocyte Chemoattractant Protein-1 receptor type B |
| MIP | Macriphage Inflammatory protein |
| Mono-Mac-1 | Cells expressing MCP-1 receptor, obtained from German Collection of Micro-organisms and Cell Cultures (DSM ACC252) |
| PBL | Peripheral Blood Leukocytes, isolated from whole blood cells obtained from healthy donors and purified by centrifugation on Ficoll-Paque(5,7 g/L). |
| PBS | phosphate-buffered saline |
| RPMI | standardmedium |
| THP-1 | Cells expressing MCP-1 receptor, ATCC TIB202 |
| TNF-α | Tumor Necrosis Factor-α |

EXAMPLE 1

Peptide Synthesis

Two peptides FDYDYGAPCHKFDVK and GLSNCESTSQLDQATQVTET covering the sequences 24–38 and 273–292, respectively, of the Monocyte Chemoattractant Protein-1 receptor type B molecule (MCP-1RB), were synthetized on an automated multiple peptide synthesizer (AS 422, Abimed) using the solid-phase procedure and standard Fmoc-chemistry in a basis of 25 μmol. The synthesis was carried out on N-α-Fmoc-protected amino acid, linked to p-benzyloxybenzyl alcohol resin (4-(Hydroxymethyl) phenoxymethyl-copoly(styrene-1% divinylbenzene) resin) (Wang resin, Novabiochem), with Fmoc-protected amino acids activated in situ with PyBOP (benzotriazole-1-yl-oxy-tris-pyrrolidino-phosphonium hexafluorphosphate) in the presence of N-methyl morpholine (NMM) and 20% piperidine/DMF for deprotection. The protecting side chain groups were as follows: Asn, Cys, Gln and His Trt); Glu and Asp (OtBu); Lys (Boc); Ser, Thr and Tyr (tBu). Peptides were cleaved from the resin with 82.5% trifluoroacetic acid (TFA) and 5% phenol, 5% $H_2O$, 5% thioanisole, 3.5% EDT as scavengers, precipitated and washed with cold methyl tert-butyl ether, water-extracted, lyophilized and purified by reverse-phase high performance liquid chromatography on Nucleosil C-18 semipreparative column (Tracer). Purity and composition of the peptides were confirmed in reverse-phase high performance liquid chromatography on C-18 Nucleosil 120 analytical column (Tracer) with a 5–70% acetonitile gradient containing 1% TFA and by amino aid analysis using a Beckman 6300 amino acid analyzer, after acid hydrolysis in a $N_2$ atmosphere for 18 h at 110° C.

EXAMPLE 2

Antigen Preparation and Immunizations 2.1 Coupling of Peptides to KLH.

Peptides MCP-1RB (24–38) and (273–292) were coupled to Keyhole Limpet Hemocyanin (KLH, Pierce) via Cys 32 and Cys 277 respectively using Sulpho-succinimidyl 4-(N-maleimido-methyl)cyclohexane-1-carboxylate (Sulfo-SMCC) as a linking agent.

KLH was activated in phosphate buffer solution pH 7.2, using a molar ratio of Sulfo-SMCC of 6000:1 for 60 min at 30° C. Activated KLH was gel-filtered through Sephadex G-25 and mixed to peptides in 0.1 M sodium phosphate pH 8.0 using a molar ratio of peptide to KLH of 3000:1 for 18 h at room temperature. The final molar ratio of peptide to carrier protein was estimated by amino acid composition of the complex relative to the amino acid composition of the carrier protein alone.

2.2. Immunization

Balb/c mice, two to three months of age, were immunized with the above described KLH-coupled peptides. Each mouse first received a sub cutaneous injection of 40 μg of peptide in 0.15 ml of phosphate-buffered saline (PBS) emulsified in 0.15 ml of Freund s complete adjuvant (Difco Laboratories, USA), (Day 0). Mice were boosted subcutaneously at days 30 and 60 with the same amount of peptide, emulsified in Freund s incomplete adjuvant. Prior to fusion, mice were boosted intravenously on days −3 and −2 with 30 μg of peptide in 0.15 ml of sterile saline.

Serum from immunized mice immunized with KLH-MCP1RB(24–38) or KLH MCP1RB(273–292) was collected 7–10 days after each boost and the presence of specific antibodies was determined in enzyme-linked immunoassay (EIA), western blot or fluorescence activated cell sorting (FACS). All mice responded to the corresponding immunogen (uncoupled synthetic peptide) in EIA, with titers (antiserum dilution giving half-maximum binding) of 1/2500–1/20000.

EXAMPLE 3

Preparation of monoclonal antibodies

In all fusion experiments, the non-secreting P3X63Ag8.653 myeloma cell line (CRL 1580, ATCC) was used. Immunized mice, selected on the basis of antibody production, were sacrificed and the spleen was aseptically removed and teased apart until most of the cells were released. Cells were transferred to RPMI 1640 (Biowhittaker) containing 10% Foetal Calf Serum (FCS), 1 mM pyruvate and 2 mM glutamine (Complete medium). Prior to fusion, red cells from the spleen were lysed using $NH_4Cl$ (0.85% in $H_2O$), and removed by centrifugation. Myeloma cells were mixed with the splenocytes in a 1:5 ratio, and the cells were washed twice by centrifugation in prewarmed medium without serum. After the final wash, 1 ml of prewarmed Polyethyleneglycol 4000 (PEG, Merck, 50% w/v in RPMI 1640) was added to the cell pellet during 1 min with gentle stirring. The PEG was diluted by slow addition of 20 ml of medium without serum (1 ml/min). The cells were then centrifugated (1000 rpm, 10 min at room temperature), resuspended in complete medium, counted and transferred to flasks at a concentration of $10^6$ cells/ml. The cells were left overnight at 37° C. in a 50% $CO_2$ atmosphere.

The fused cells were centrifugated and resuspended in complete medium containing azaserine and hypoxanthine ($10^{-5}$ and $10^{-4}$ M respectively, Sigma Chemical Co.) and plated at a density of $10^4$ cells/well in 96 well tissue culture plates over thymocytes as feeder layer. In most cases only part of the fusion was plated, and the rest of the fusion was frozen. After 12–14 days supernatants from wells with growing hybrids were tested for the presence of specific antibodies (see below in Example 4.).

Wells containing positive hybrids were transferred to 24 well plates in complete medium containing hypoxanthine. Those hybrids which produced antibodies that were considered of interest, were stabilized by cloning by limiting dilution, until a stable antibody production was achieved.

Both supernatants from hybrids growing in serum-free medium and ascites fluid obtained from pristane-injected mice were used as source of antibodies.

EXAMPLE 4

Screening and Characterization of the Monoclonal Antibodies 4.1. Antibody capture enzyme-linked immunoassay (EIA)

The synthetic peptides MCP1RB (24–28) and (273–292) (3 μg/ml in PBS, 100 ml/well) were adsorbed on microtiter plates (Maxi-sorb, Nunc) overnight at 4° C. Remaining protein binding sites were blocked with 0.5% BSA in PBS (200 μl/well, 60 min at 37° C.). After washing the plates with destilled water, monoclonal antibodies were incubated for 60 min at 37° C., followed by a peroxidase-labeled goat anti-mouse immunoglobulin antibody (GAM-PO, Tago Inc.) and OPD (Sigma Chemical Co.). The reaction was stopped with 3N sulphuric acid and the optical density determined at 492 nm.

4.2. Isotype Determination.

The isotype of each antibody was determined in EIA, using solid-phase adsorbed affinity-purified goat anti-mouse immunoglobulins antibody (2.5 μg/ml in PBS, 100 μl/well), overnight at 4° C. After blocking with BSA, the monoclonal antibodies were incubated for 60 min at 37° C., followed by subclass-specific anti-mouse Ig, peroxidase-labeled antibodies (Southern Biotechnologies Associates, Inc. USA) and OPD. The reaction was stopped with 3N sulfuric acid and optical densities determined at 492 nm.

4.3. Fluorescence Activated Cell Sorting Analysis (FACS analysis).

THP-1 or Mono-Mac-1 cells, expressing the MCP-1 receptor, were centrifugated (1000 rpm, 10 min at room temperature), plated in V-bottom 96-well plates (250,000 cells/well), and incubated with 50 μl/well of the different undiluted supernatants (from Example 3) for 60 min at 4° C. Cells were washed twice with PBS containing 2% BSA and 2% FCS by centrifugation (750 rpm, 5 min at 4° C.). Goat anti-mouse-FITC conjugate was then added and incubated for 30 min at 4° C. and washed twice. Cell-bound fluorescence was determined in a Profile XL flourescence activated cell sorter.

4.4. Calcium Determinations.

Changes in intracellular calcium concentration were monitored using the fluorescent probe Fluo-3 (Calbiochem). Mono-Mac-1 cells ($2.5 \times 10^6$ cells/ml) were resuspended in complete medium containing 10 nM HEPES and incubated with 2 ml/$10^6$ cells of Fluo-3 (250 mM in DMSO) for 15 min at 37° C. After incubation cells were washed and resuspended in complete medium containing 2 mM $CaCl_2$ and kept at 37° C. before a range of different ligand concentrations were added (chemokine or monoclonal antibody in PBS). Calcium release, in response to cytokines of monoclonal antibody was determined in FACS at 525 nm, showing the binding of the receptor to the ligand.

For determination of the antagonistic activity of the corresponding mAb, Mono-Mac-1 cells were preincubated with various concentrations of ammonium sulfate-purified antibodies in RPMI (standard medium) for 30 min at 4° C. After washing, cells were loaded with Fluo-3 and Calcium release was determined, as above.

4.5. Immunoprecipitation and Western Blot

Mono-Mac-1 cells, THP-1 cells, human PBL and rat spleen cells were centrifugated and resuspended in 50 mM Tris, 50 mM NaCl, 5 mM DTT buffer containing a cocktail of protease inhibitors. Cell were subjected to 3–5 cycles of freezing (in liquid nitrogen) and thawing. Cells were then centrifugated at 1500 rpm for 2 min at 4° C., and the pellet discarded. The remaining supernatant was centrifugated at 12500 rpm at 4° C. for 15 min, and the pellet resuspended in PBS. Lysates were run under reducing conditions on 12.5% (w/v) SDS-polyacrylamide gels according to the method of Laemmli U K et al (Nature 227, 680–85, 1970). Gels were transferred to nitrocellulose on a semi-dry blotter (Bio-Rad) for 60 min at 250 mA in a 48 mM Tris base, 39 mM glycine, 20% methanol buffer containing 0.037% SDS. After blocking the membrane with 10% non-fat dry milk in PBS, the monoclonal antibodies were incubated with agitation for 120 min at room temperature, followed by a 1/5000 diluted peroxidase labelled goat anti-mouse immunoglobulins antibody (ICN). The blot was developed using ECL (Amersham), following the manufacturer instructions.

Immunoprecipitation was performed as described (30). Briefly, protein extracts were precleared by incubation with 20 $\mu$g/$10^7$ cells of anti-mouse IgG-agarose (Sigma) for 60 min at 4° C. and centrifugation (1 min, 15,000 xg). The supernatant was then incubated with mAb MCP-1R03 (5 mg/ml in PBS) for 90 min at 40° C., followed by incubation with 20 $\mu$g/$10^7$ cells of anti-mouse IgG-agarose for 60 min. Samples were centrifuged at 15,000 xg for 15 min at 4° C. and the agarose pellet washed twice with lysis buffer and three times with 50 mM Tris HCl, pH 7.6 (15,000 xg, 1 min at 4° C.), resuspended in Laemmli buffer and electrophoresed.

4.6. Purification of Antibodies

Antibodies were purified by 50% ammonium sulphate precipitation and/or affinity chromatography on immobilized protein A Sepharose (Pharmacia, Sweden) of ascites fluids or supernatants from corresponding hybrids grown in serum-free medium (0–1% FCS in Ultradoma medium, Gibco).

4.7. Chemotaxis.

Nycoprep™ purified human monocytes of Mono-Mac-1 cells were placed in the upper well of 24 well transmigration chambers (Transwell, Costar, Cambridge Mass.), which were previously coated with mouse brain endothelial cells (50.000 cells/well, 48 hours at 37° C., 5% $CO_2$ or hasta confluencia). Chemokines or agonist antibody were added to the lower well, diluted in RPMI, 0.25% BSA. Plates were incubated for 120 min at 37° C., 5% $CO_2$, the inerts were then removed from the wells and cell migrated to the lower chamber were counted.

For blocking of MCP-1-induced chemotaxis, different concentrations of purified mAb in PBS were added to the upper well, simultaneously with the addition of chemokines to the lower well. The chemotaxis was followed as above.

EXAMPLE 5

Results

Two of the sera recognized Mono-Mac-1 cells in FACS (table I) and the corresponding mice were subsequently used for cell fusions. After fusion, hybrids producing antibodies which bind the uncoupled synthetic peptide in EIA, and gave positive results in FACS were selected and stabilized (Table II).

Six stabilized monoclonal antibodies were characterized in order to determine their capacity to recognize the MCP-1 receptor in lysates of Mono-Mac-1 cells by immunoprecipitating the MCP-1 receptor as well as in western blot. Furthermore their ability to act as agonist or antagonist of the MCP-1 was also characterized.

The main characteristics of these mAb are summarized in table III. All six mAb recognize Mono-Mac-1 and THP-1 cells in FACS (FIG. 1). The X-axis indicates the logarithm of relative fluorescence intensity, and the Y-axis indicates relative cell number.

The protein recognized by western blot correspond to a 32 kDa protein in the t-cell types employed (human monocytic cell lines and human monocytes). Western blot analysis show that MCPR-02 and MCPR-05 are capable of binding the human and rat MCP-1 receptor immobilized on cellulose membrane.

All six mAb recognize THP-1 and Mono Mac 1 cells in flow cytometry analysis. One, MCPR-05, also recognizes a specific 32 kDa band in both cell lines, as well as in PBL and tonsil-derived lymphocytes, in western blot analysis, which is displaced by the (273–292) peptide; mAb MCPR-03 immunoprecipitates the same 32 kDa protein from Mono Mac 1 cells. Monoclonal antibody specificity for CCR2 was previously demonstrated in western blot and flow cytometry analysis using CCR2-transfected 293 cells, known not to express the CCR2 chemokine receptors, as well as in Jurkat cells, which express several chemokine receptors (CCR3, CCR5 and fusin) but not CCR2. While neither cell line is recognized by any of these antibodies in flow cytometry or western blot, both are clearly positive after being transfected with the CCR2 gene.

Flow cytometry analysis of human PBLs indicate that these mAb recognize CD-11b, PBLs. One mAb, MCPR-05, also recognizes rat peripheral blood leukocytes and splenocytes, staining positive with the monoclonal antibodies ED1 and ED2 (Serotec). The mouse monoclonal antibody ED1 recognizes rat monocytes and macrophages, whereas the mouse monoclonal antibody ED2 recognizes rat macrophages.

Figure 2:
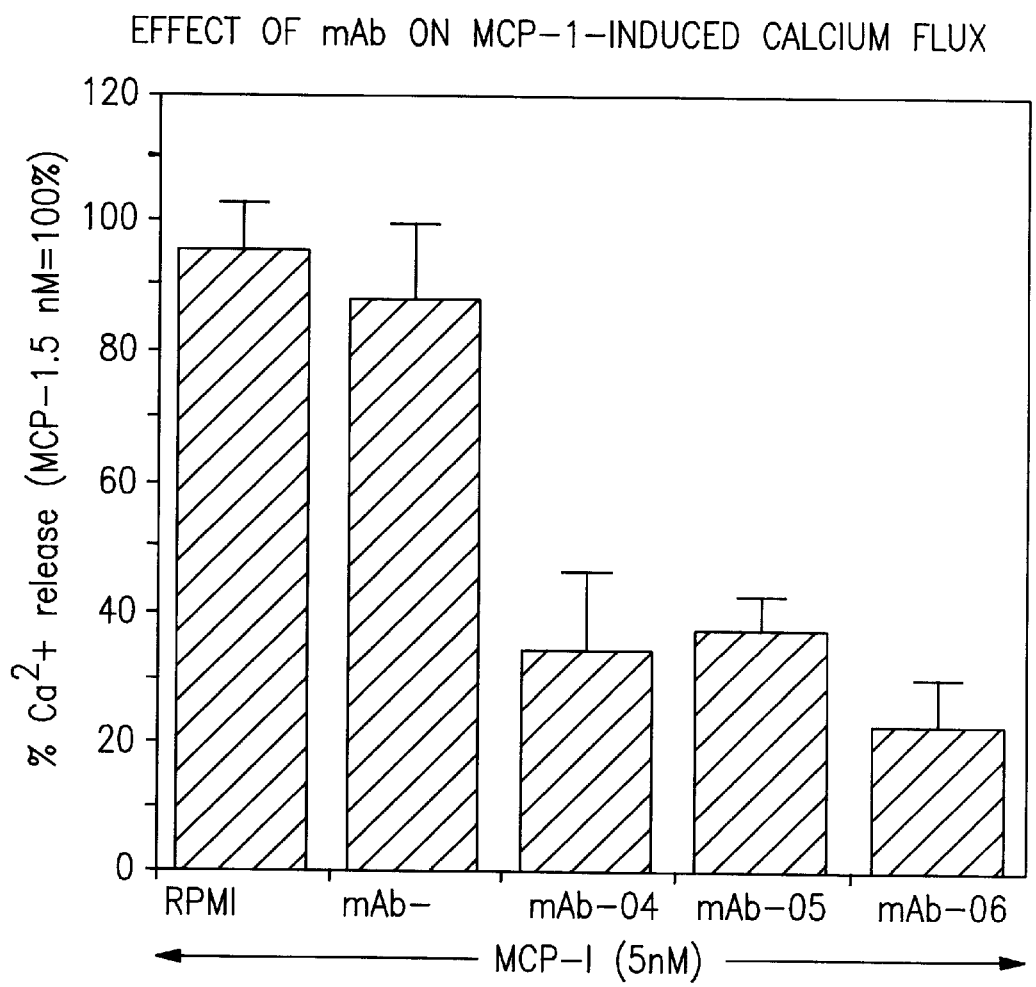
FIG. 2 illustrates MCP-1 induced calcium release in Mono-Mac-1 cells and the effects of the preincubation with an irrelevant monoclonal (mAb-), the monoclonal antibody MCPR-04, the monoclonal antibody MCPR-05 and the monoclonal antibody MCPR-06.

Three mAb (MCPR-04, -05 and -06) act as antagonists of the receptor, as they block the MCP-1-induced calcium flux in Mono-Mac-1 cells (FIG. 2). The antibodies with antagonistic activity recognize the third extracellular loop of the receptor (aa 273–292) while the agonistic antibody recognizes the amino terminal region (aa 24–38).

Figure 3A:
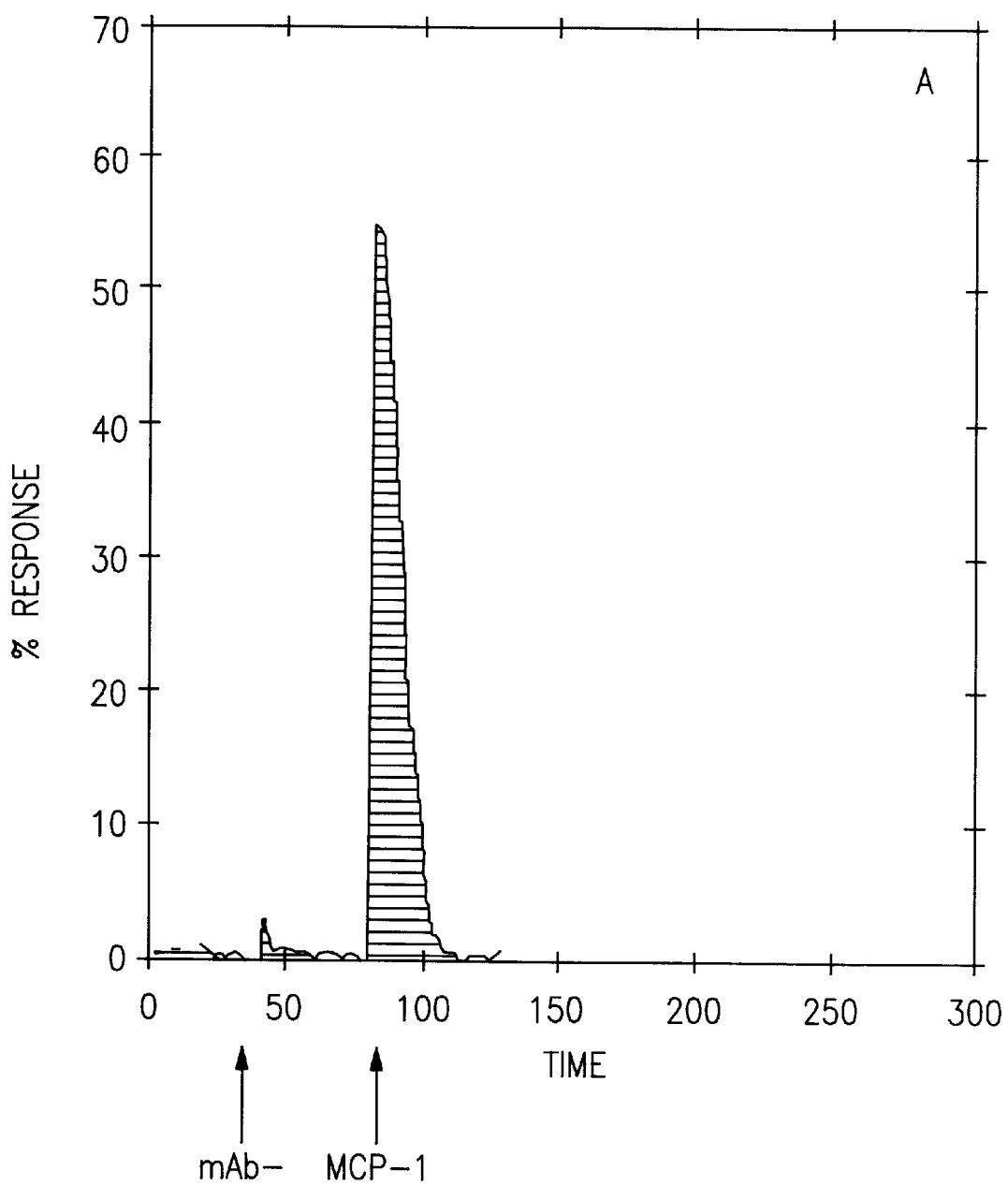
FIGS. 3a to 3f show the mobilization of $Ca^{2+}$. Mono-Mac-1 cells, loaded with Fluo-3 were stimulated sequentially with 100 nM of an irrelevant monoclonal antibody (FIG. 3a) or MCPR-04 (FIG. 3b) followed by 5 nM MCP-1. In other cases cells were preincubated for 30 min at 4° C. with the same concentration of an irrelevant monoclonal antibody (FIG. 3c) or MCPR-05 (FIG. 3d) prior to stimulation with MCP-1. Loaded cells were challenged with an irrelevant mAb (FIG. 3e) or MCPR-01 (FIG. 3f), followed by 5 nM MCP-1.
Figure 3B:
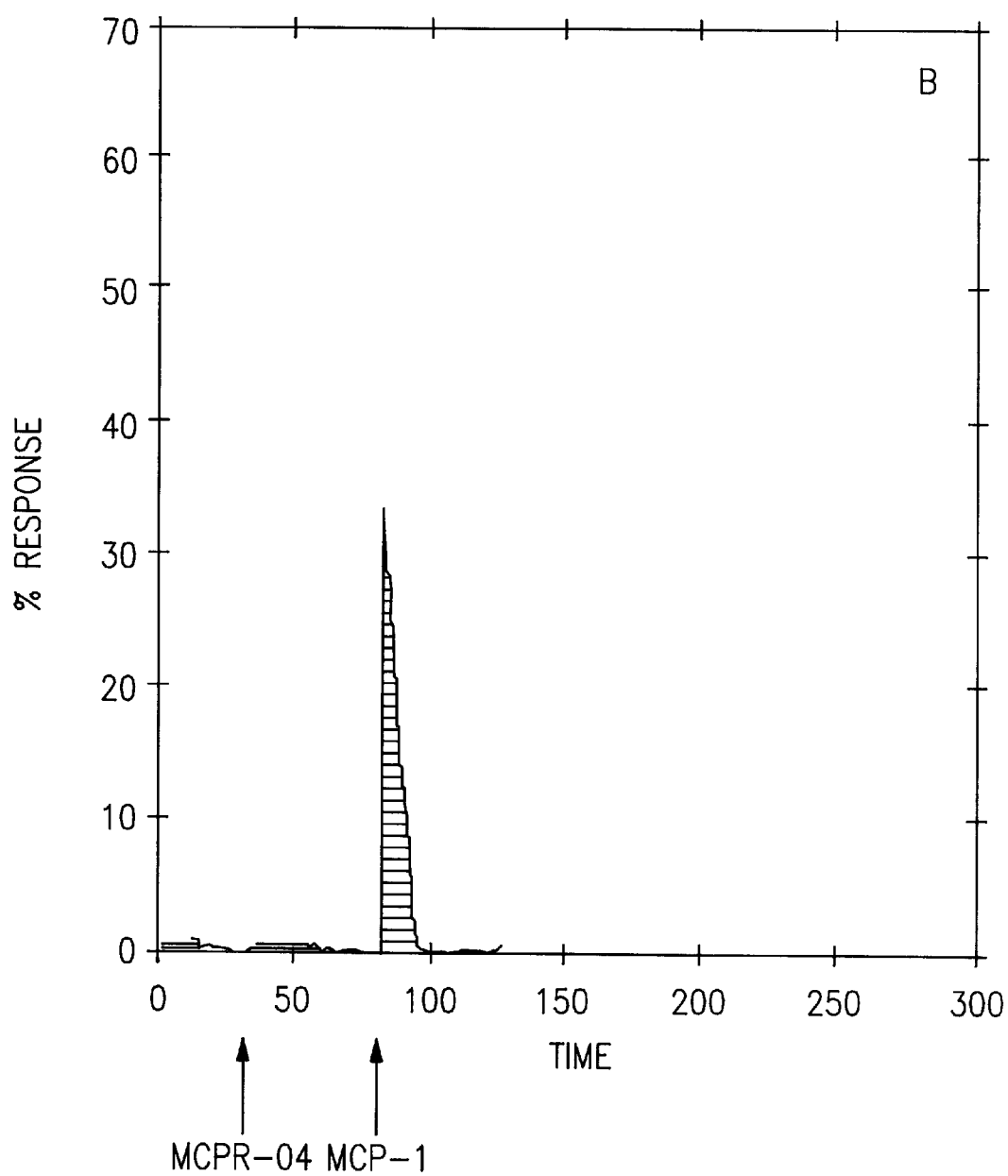
Figure 3C:
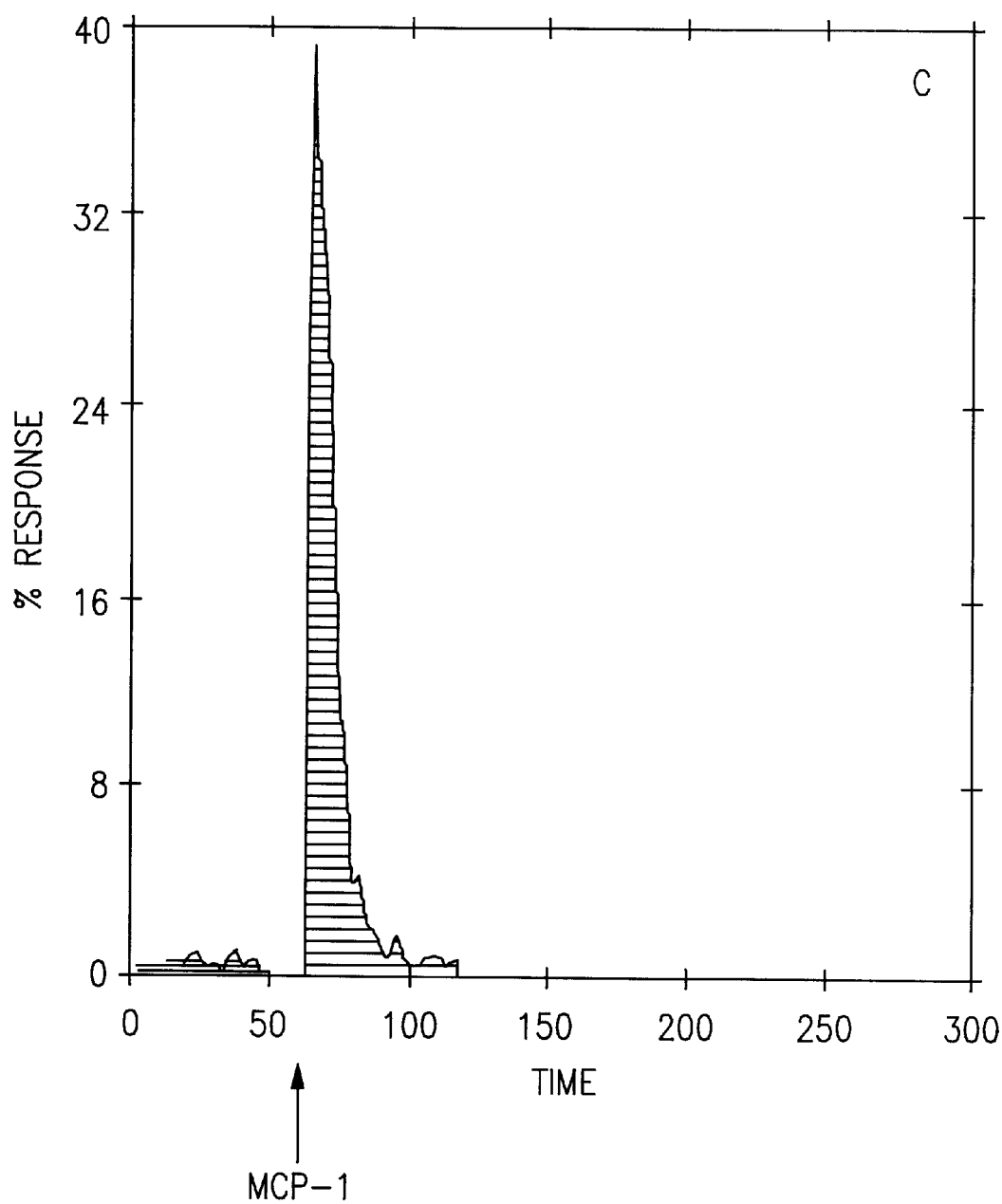
Figure 3D:
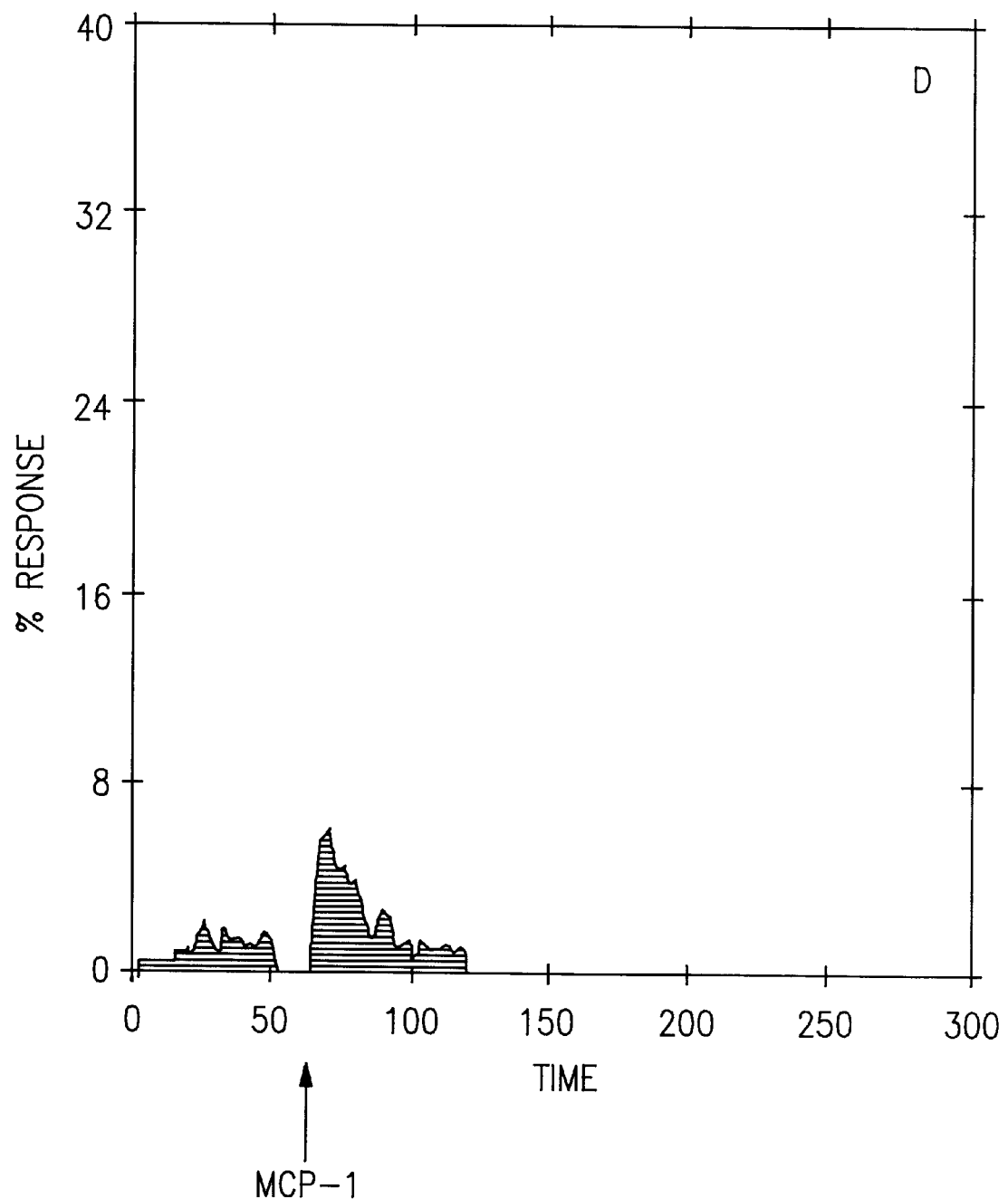
Figure 3E:
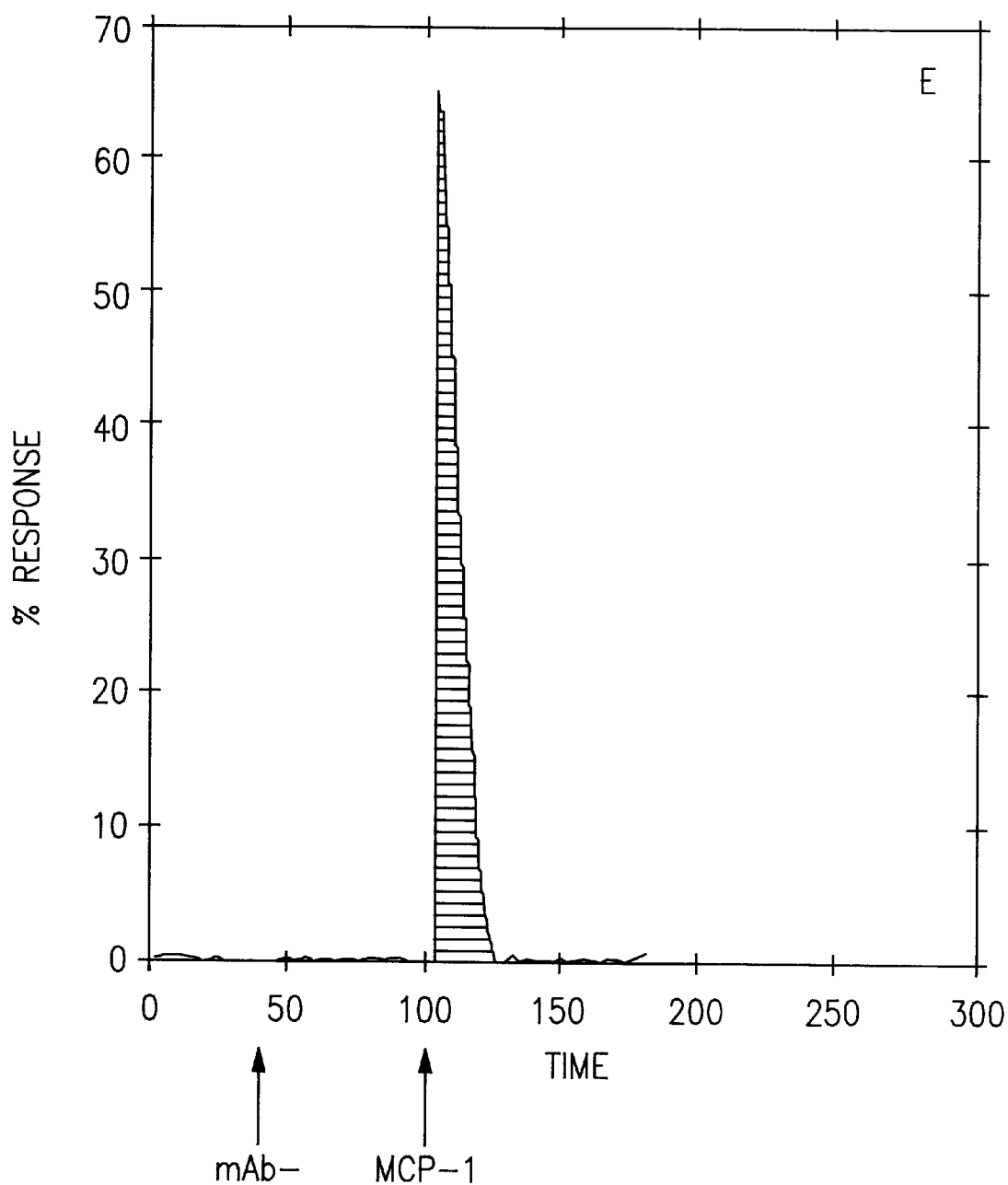
Figure 3F:
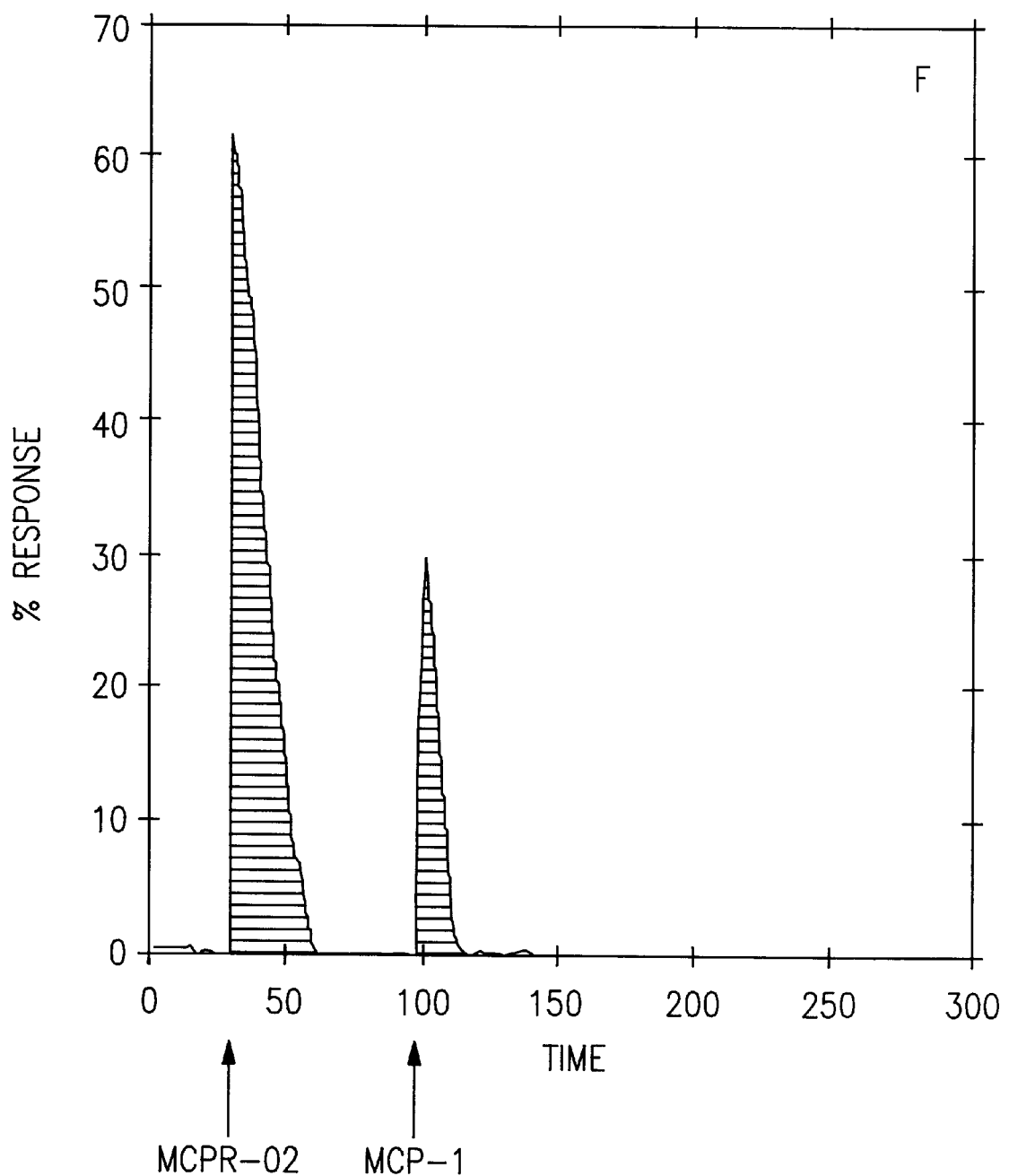

One mAb (MCPR-02) act as agonist of the MCP-1 receptor, based on calcium determinations. A rapid and transient rise in $Ca^{2+}$ concentration was seen in Mono-Mac-1 cells after stimulation with mAb MCPR-02. The pre-treatment of the cells with this mAb led to a marked decrease of responsiveness to MCP-1, showing that the calcium response is desensitized (FIG. 3f).

Figure 4A:
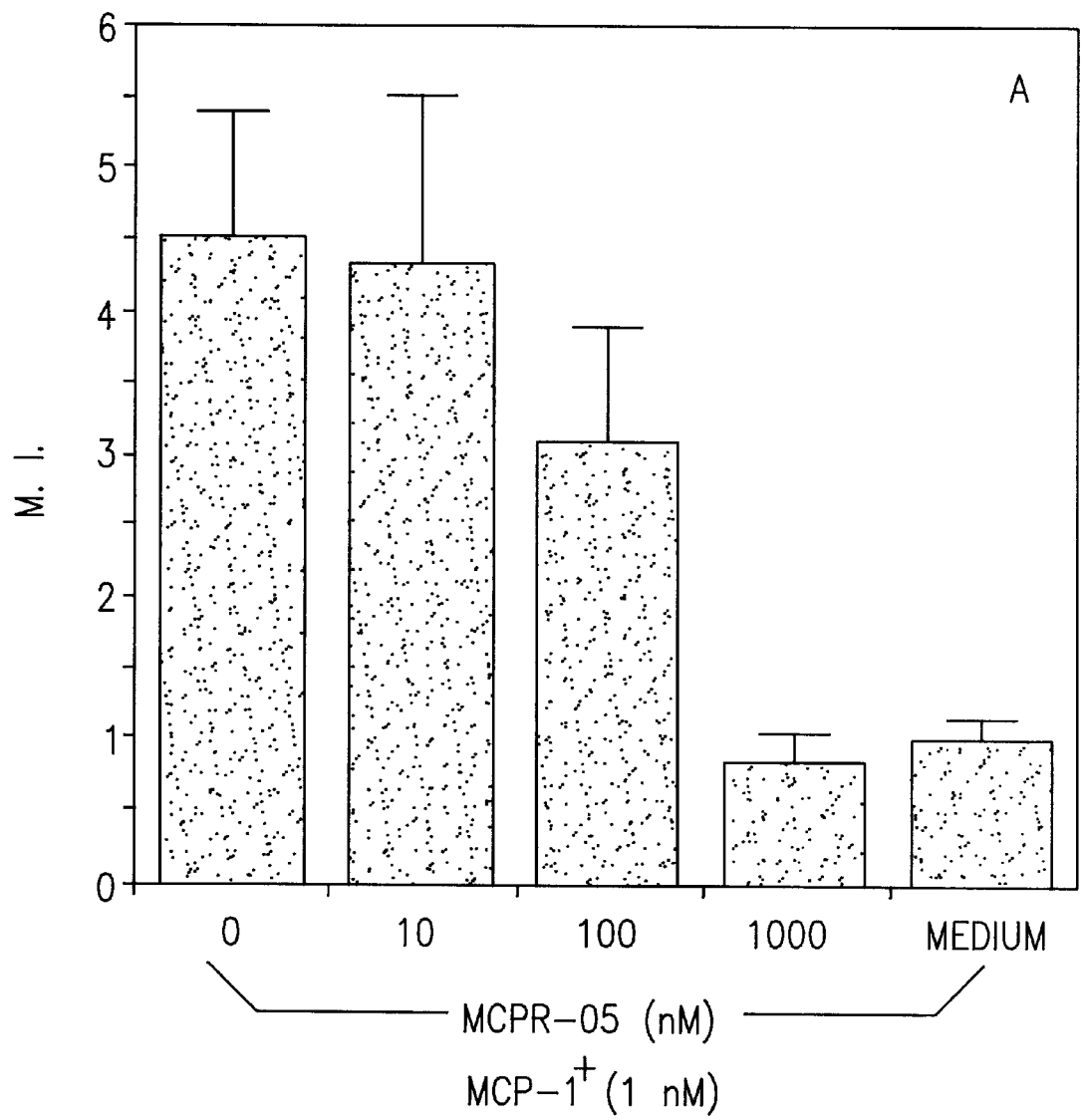
FIGS. 4a and 4b. Chemotaxis. Mono-Mac-1 cells were preincubated with several concentrations of MCPR-05 and placed on the upper chamber of endothelial cell-coated transwells and MCP-1 (1 nM) added to the lower well (FIG. 4a). Cells migrated to the lower well were counted and expressed as a Migration Index (M.I.), which was calculated as the x-fold increase in migration observed over the negative control (Medium).
Figure 4B:
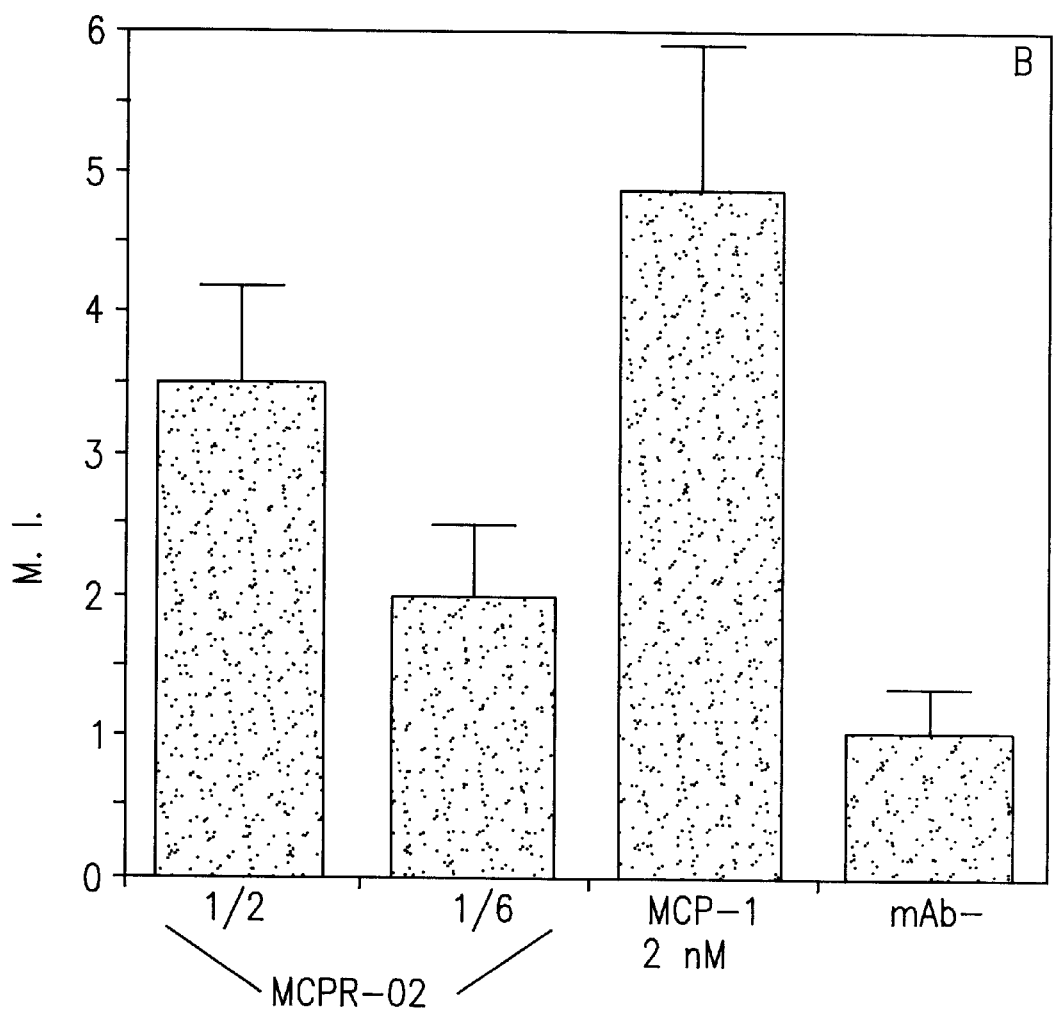

Chemotaxis. Mono-Mac-1 cells were preincubated with several concentrations of MCPR-05 and placed on the upper chamber of endothelial cell-coated transwells and MCP-1 (1 nM) added to the lower well (FIG. 4a). Cells migrated to the lower well were counted and expressed as a Migration Index (M.I.), which was calculated as the x-fold increase in migration observed over the negative control (Medium). For the concentration of 100 and 1000 nM a significant reduction of the chemotaxis of Mono Mac 1 cells could be observed for the antagonistic antibody MCPR-05. FIG. 4b shows the effect of MCPR-02 mAb dilution on Mono-Mac-1 cells migration under the same condition.

CCR2 is expressed in monocytes, resting B cells and activated T cells.

Figure 5A:
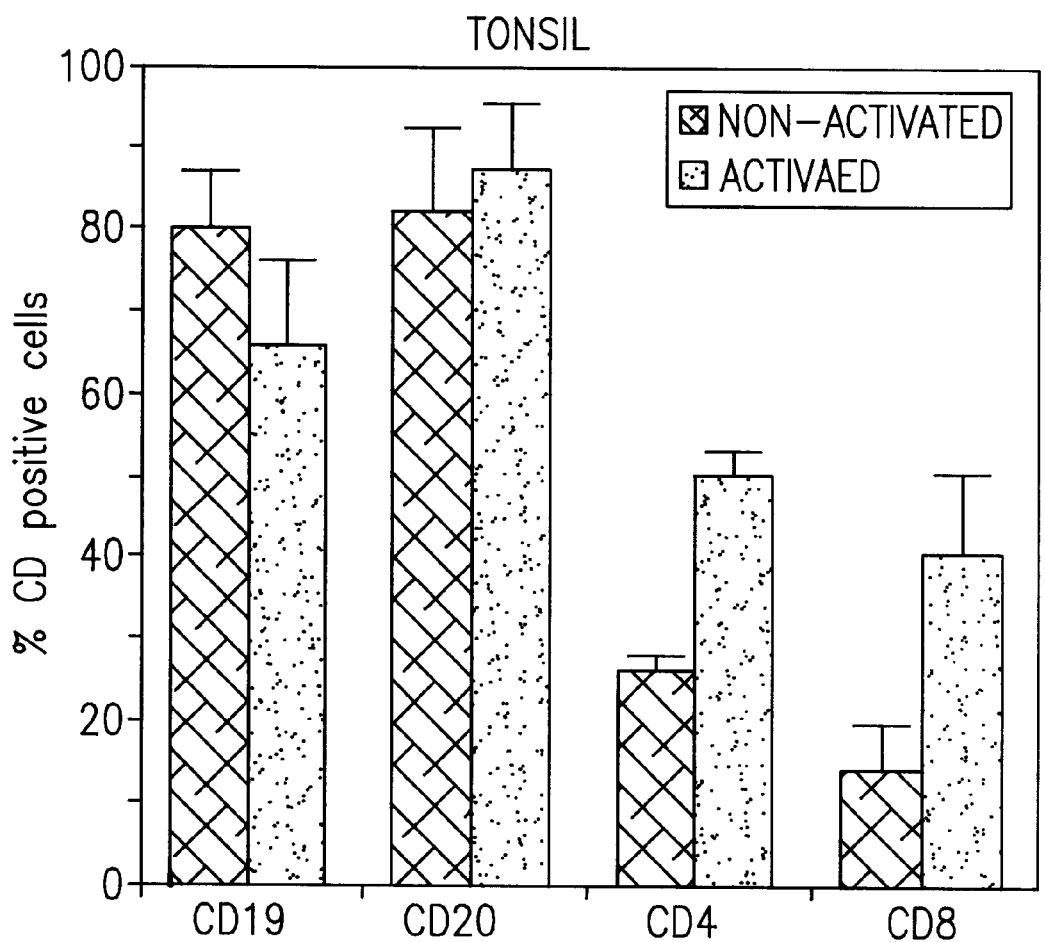
FIGS. 5a and 5b. CCR2 receptor expression on human leukocytes. CCR2 chemokine receptor expression in resting (−) or activated (+) PBL or tonsil-derived cells (FIG. 5a), using double-color staining with MCPR-05 and anti-T(CD4) or anti-B (CD19, CD20) antibodies, as indicated. Percentage of cells expressing the CCR2 receptor, as defined by MCPR-05 binding in flow cytometry in various lymphocyte populations defined the indicated CD markers.
Figure 5B:
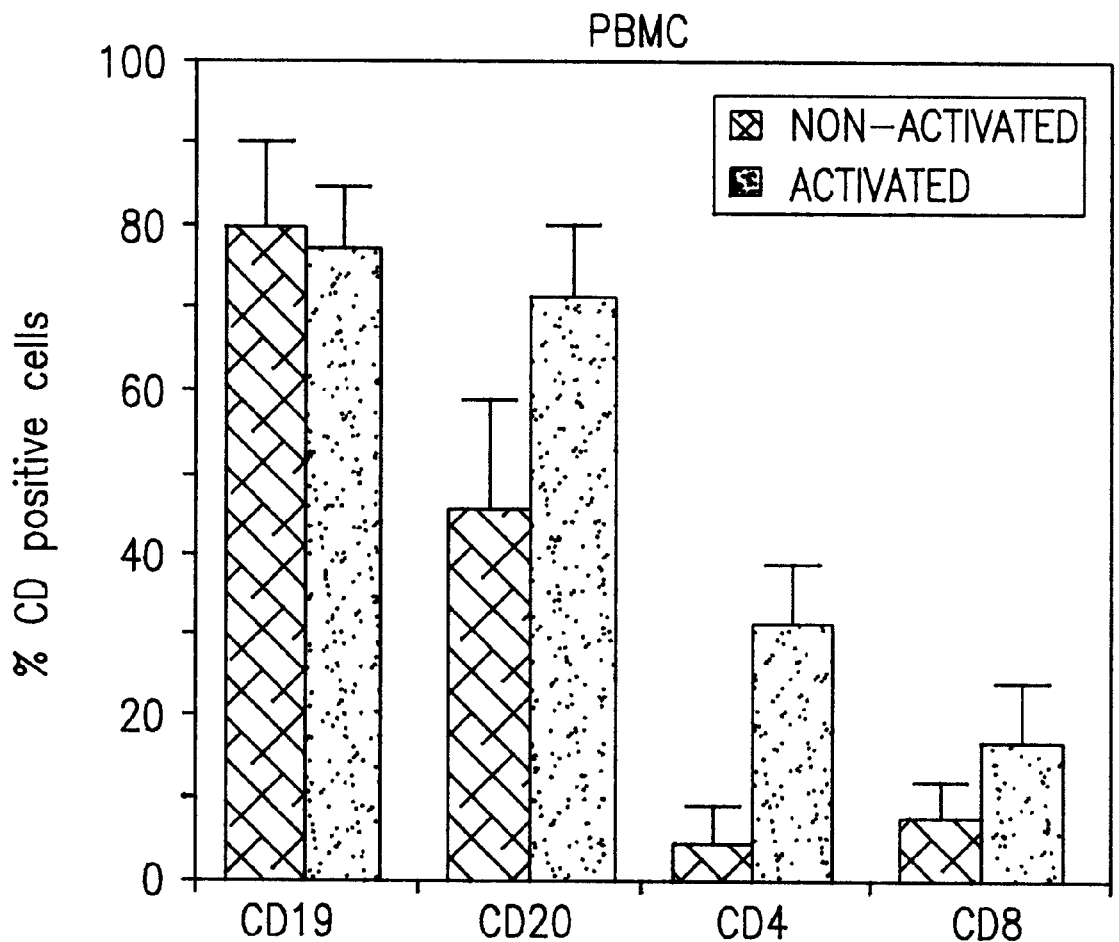

Based on the specificity of these mAb, we have established the population of human peripheral blood mononuclear cells expressing the CCR2. Resting as well as PHA- or ionophore-activated PBMC were tested in flow cytometry using double-color staining in conjunction with markers specific for monocyte/macrophages, B cells and T cells. In untreated cells, the mAb recognized 100% of the $CD11b^+$, $CD13^+$ and $CD14^+$ cells in the monocyte/macrophage population, based on forward and side scatter analysis. Anti-CCR2 antibodies bound to 50% of all $CD19^+$ cells, while trace binding or no binding at all was observed in $CD3^+$ cells. This indicates CCR2 chemokine receptor expression in monocytes and B cells, but not in T cells. Resting and activated tonsil-derived lymphocytes were used to confirm these data, showing that indeed all monocytes/macrophages and the majority of B cells in spleen and tonsils are stained by anti-CCR2 antibodies (FIGS. 5a and 5b). Following activation, 30–45% of CD4$^+$ and 20–40% of CD8$^+$ cells express the CCR2 receptor, while its expression is unaltered in tonsil and peripheral blood B cells, indicating activation-dependent CCR2 expression in T cells. No modifications in receptor expression are seen in B cells upon activation, despite its origin in PBL or tonsil. FIGS. 5a and 5b summarizes the cell populations that express the CCR2 chemokine receptor in tonsil and PBL.

Figure 6A:
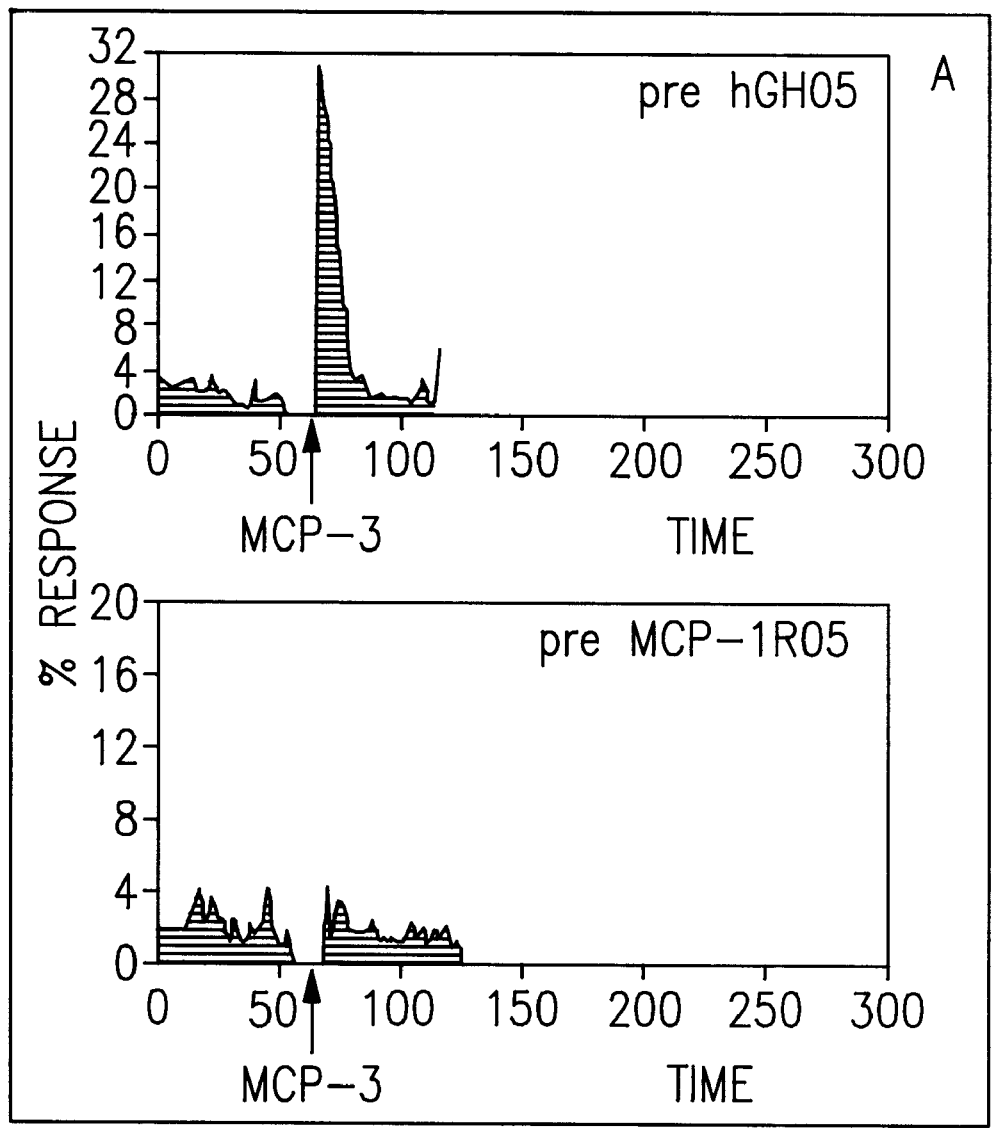
FIGS. 6a to 6c. Effect of preincubation with the antagonist mAb MCPR-05 on MCP-3-induced $Ca^{2+}$ influx (A, B) and transmigration (C) of cells.
Figure 6B:
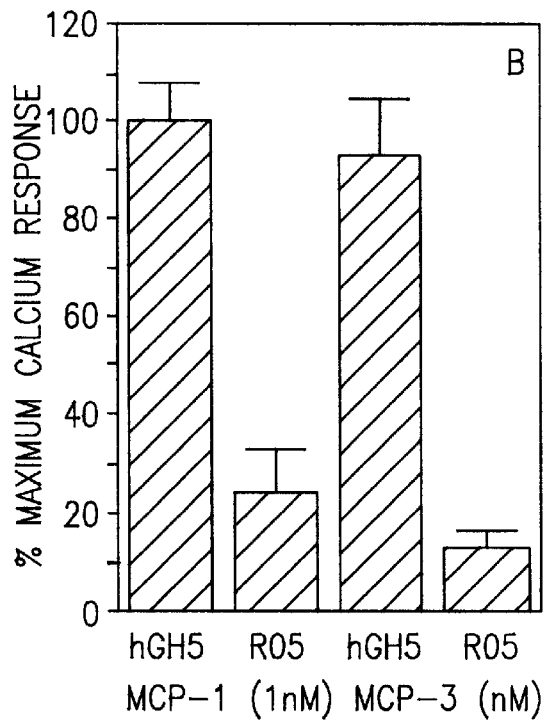
Figure 6C:
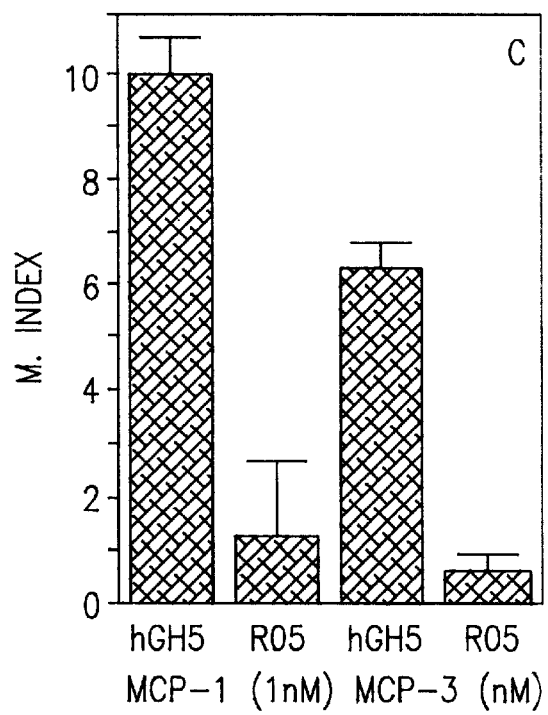

FIGS. 6a to 6c shows that MCPR-05 blocks MCP-3-induced Ca$^{2+}$ influx and transmigration of Mono Mac 1 cells. Calcium influx was induced, using 3 nM MCP-3. Effect of preincubation with the antagonist mAb MCPR-05 on MCP-3-induced Ca$^{2+}$ influx is shown in FIGS. 6a and 6b and transmigration i shown in FIG. 6c of these cells, as compared to that of an isotype-matched control mAb (hGH5). Results correspond to the mean of triplicates of a representative experiment.

The Mono-Mac-1 antagonistic antibody MCPR-02 elicited a significant chemotactic response of Mono-Mac-1 cells at dilution of 1/2 and 1/6.

Discussion

We have thus obtained mAb which are able to neutralize the MCP-1 activity and mAbs which mimic the MCP-1 activity. These two properties are clearly differentiated to two regions of the MCP-1 receptor. The blocking mAb recognize sequences present in the third extracellular loop of the receptor, which could correlate to regions involved in the binding of MCP-1, while agonist activity map to the N-terminal region of the receptor, and should correlate with regions needed for the function of the receptor.

We have thus found antibodies capable of binding to the MCP-1 receptor and among which some are agonists (MCPR-02) and some are antagonists (MCPR-04, MCPR-05 and MCPR-06). These findings must be regarded as very surprising and are very interesting and promising in the use as a medicament. All described antibodies recognizing the MCP-1 receptor can be useful for in vivo diagnostic purposes.

Two of the antibodies found (MCPR-02 and MCPR-05) are capable of binding the MCP-1 receptor in immunoprecipitation in context of a biological tissue and also recognizing the receptor adsorbed to an artificial membrane in immunoblotting experiments. The antibodies can be useful for in vitro diagnostic purposes involving immobilized antigens.

We describe thus a panel of monoclonal antibodies specific for the human CCR2, derived using synthetic peptides of the third extracellular domain (amino acid residues 273–292) and amino terminal region (residues 24–38) of this receptor. In flow cytometry and western blot analyses, these mAb recognize CCR2-transfected Jurkatt and 293 cells, while there is no recognition of mock-transfected cells. It has recently been shown that several CC (CCR2, 3, 4 and 5) and CXC (fusin) chemokine receptors act as the coreceptors required for cell fusion and HIV infection of cells. This has increased interest in this receptor family as possible targets for the prevention of the consequences of HIV infection (22–27). We have also described that CCR2 acts as an HIV-1 coreceptor, showing that MCP-1 displays HIV-1 neutralizing activity (submitted). In addition, the MCPR-02 mAb promotes HIV-1 neutralization, while the MCP-1 antagonist mAb MCPR-05 does not neutralize the virus, but effectively blocks MCP-1-induced neutralization. Since the MCPR-04 and -R105 mAb do not block HIV infection, these data indicate that HIV-1 interacts with the NH2 terminal domain of the CCR2 receptor. Finally, since mAb MCPR-02 as well as the MCP-1 chemokine block HIV-1 infection, we would advocate that HIV-1 interacts with the inactive the receptor form, but not with the active form.

TABLE I

| IMMUNOGEN | # MOUSE | EIA[1] | W. Blot[2] | FACS[3] |
|---|---|---|---|---|
| MCP1-RB | 1 | + | − | − |
| (24–38)-KLH | 2 | + | − | − |
|  | 3 | + | + | + |
|  | 4 | + | − | − |
| MCP1-RB | 1 | + | + | + |
| (273–292)-KLH | 2 | + | + | − |
|  | 3 | + | + | − |

[1]EIA using solid phase-adsorbed uncoupled synthetic peptide.
[2]Using membranes from mono mac-1 or THP-1 cells.
[3]Flow cytometry analysis of mono mac-1 and THP-1 cells.

TABLE II

| FUSION NAME | IMMUNOGEN | +/grown in EIA[1] | + in FACS[2] |
|---|---|---|---|
| XB | MCP1-RB(24–38)-KLH | 2/384 | 2 |
| WZ | MCP1-RB(273–292)-KLH | 23/444 | 4 |

[1]EIA using solid phase-adsorbed uncoupled synthetic peptide.
[2]Flow cytometry analysis of mono mac-1 and THP-1 cells.

TABLE III

| mAb | Specificity[1] | Isotype | W. blot[2] | FACS[3] | Chemotaxis[5] | | Ca$^{2+}$Flux[4] | |
|---|---|---|---|---|---|---|---|---|
|  |  |  |  |  | Agonist | Antagonist | Agonist | Antagonist |
| MCPR-01 | (24–38) | G2a | − | + | − | − | − | − |
| MCPR-02 | (24–38) | G2a | + | + | + | − | + | − |
| MCPR-03 | (273–292) | G1 | − | + | − | − | − | − |
| MCPR-04 | (273–292) | G2a | − | + | − | + | − | + |
| MCPR-05 | (273–292) | G2b | + | + | − | + | − | + |
| MCPR-06 | (273–292) | G2a | − | + | − | +/− | − | + |

[1]Sequence of the MCP-1 receptor type B recognized by the corresponding mAb.
[2]Recognition of mono mac-1 cell lysates under reducing conditions.
[3]Flow cytometry analysis of monomac-1 cells.
[4]Effect of the corresponding mAb on MCP-1 induced calcium flux in monomac-1 cells.
[5]Effect of the different mAb on MCP-1 induced chemotaxis on transwells coated with endothelial cells.

What is claimed is:

1. An agonist antibody that binds to the amino terminal portion of the extracellular domain of the monocyte chemoattractant protein-1 chemokine receptor CCR2.

2. The antibody according to claim 1, wherein the extracellular sequence comprises amino acid residues 24–38 of the amino terminal region of the receptor.

3. The antibody according to claim 1, wherein the antibody is a monoclonal antibody.

4. The antibody according to claim 1, wherein the antibody immunoprecipitates the monocyte chemoattractant protein-1 chemokine receptor CCR-2 in the context of cells or biological tissue.

5. The antibody according to claim 1, wherein the antibody detects the monocyte chemoattractant protein-1 chemokine receptor CCR-2 adsorbed on an artificial membrane.

6. The antibody according to claim 1, wherein the antibody recognizes Mono-Mac-1 cells and THP 1 cells that express the monocyte chemoattractant protein-1 chemokine receptor CCR-2.

7. The antibody according to claim 1, further comprising:
a label to detecting the antibody, the label being selected from the group consisting of radioactive labels, fluorescence labels, enzymatic labels, and affinity tags.

8. An antagonist antibody that binds to the extracellular sequence comprising the third extracellular domain of the monocyte chemoattractant protein-1 chemokine receptor CCR2.

9. The antibody according to claim 8, wherein the extracellular sequence comprises amino acid residues 273–292 of the third extracellular loop of the receptor.

10. The antibody according to claim 8, wherein the antibody acts as an antagonist for chemotaxis or $Ca^{2+}$ flux.

11. The antibody according to claim 8, wherein the antibody is a monoclonal antibody.

12. The antibody according to claim 8, wherein the antibody immunoprecipitates the monocyte chemoattractant protein-1 chemokine receptor CCR-2 in the context of cells or biological tissue.

13. The antibody according to claim 8, wherein the antibody detects the monocyte chemoattractant protein-1 chemokine receptor CCR-2 adsorbed on an artificial membrane.

14. The antibody according to claim 8, wherein the antibody recognizes Mono-Mac-1 cells and THP 1 cells that express the monocyte chemoattractant protein-1 chemokine receptor CCR-2.

15. The antibody according to claim 8, further comprising:
a label to detecting the antibody, the label being selected from the group consisting of radioactive labels, fluorescence labels, enzymatic labels, and affinity tags.

16. A pharmaceutical preparation, comprising:
an agonist antibody that binds to the amino terminal portion of the extracellular domain of the monocyte chemoattractant protein-1 chemokine receptor CCR2; and
a pharmaceutically acceptable carrier.

17. A pharmaceutical preparation, comprising:
an antagonist antibody that binds to the extracellular sequence comprising the third extracellular domain of the monocyte chemoattractant protein-1 chemokine receptor CCR2; and
a pharmaceutically acceptable carrier.

18. A cell line, comprising:
cells capable of producing an agonist antibody that binds to the amino terminal portion of the extracellular domain of the monocyte chemoattractant protein-1 chemokine receptor CCR2.

19. A cell line, comprising:
cells capable of producing an antagonist antibody that binds to the extracellular sequence comprising the third extracellular domain of the monocyte chemoattractant protein-1 chemokine receptor CCR2.

20. An antibody, comprising:
an agonist antibody that binds to the amino terminal portion of the extracellular domain of the monocyte chemoattractant protein-1 chemokine receptor CCR2, thereby triggering responses associated with binding of the CCR-2 chemokine to the extracellular sequence of the receptor.

21. An antibody, comprising:
an antagonist antibody that binds to the extracellular sequence comprising the third extracellular domain of the monocyte chemoattractant protein-1 chemokine receptor CCR2, thereby blocking responses associated with binding of the CCR-2 chemokine to the extracellular sequence of the receptor.

* * * * *

UNITED STATES PATENT AND TRADEMARK OFFICE
CERTIFICATE OF CORRECTION

PATENT NO.    : 6,084,075
DATED         : July 4, 2000
INVENTOR(S)   : Peter Lind et al.

It is certified that error appears in the above-identified patent and that said Letters Patent is hereby corrected as shown below:

<u>Title page,</u>
Item [73], should read as follows:

-- [73]  Assignee:  Consejo Superior de Investigaciones, Madrid, Spain --

Signed and Sealed this

Seventeenth Day of June, 2003

JAMES E. ROGAN
*Director of the United States Patent and Trademark Office*